United States Patent
Ivri et al.

(10) Patent No.: US 12,186,234 B2
(45) Date of Patent: Jan. 7, 2025

(54) TOPICAL OCULAR DELIVERY METHODS AND DEVICES FOR USE IN THE SAME

(71) Applicant: Bausch + Lomb Ireland Limited, Dublin (IE)

(72) Inventors: Yehuda Ivri, Newport Coast, CA (US); Mark S. Blumenkranz, Portola Valley, CA (US); Peter Noymer, Los Gatos, CA (US); Daniel V. Palanker, Sunnyvale, CA (US)

(73) Assignee: Bausch + Lomb Ireland Limited, Dublin (IE)

( * ) Notice: Subject to any disclaimer, the term of this patent is extended or adjusted under 35 U.S.C. 154(b) by 0 days.

(21) Appl. No.: 16/444,894

(22) Filed: Jun. 18, 2019

(65) Prior Publication Data

US 2019/0314195 A1    Oct. 17, 2019

Related U.S. Application Data

(63) Continuation-in-part of application No. PCT/US2019/027018, filed on Apr. 11, 2019.
(Continued)

(51) Int. Cl.
*A61F 9/00* (2006.01)
*A61K 9/00* (2006.01)
(Continued)

(52) U.S. Cl.
CPC .......... *A61F 9/0008* (2013.01); *A61K 9/0048* (2013.01); *A61K 31/135* (2013.01);
(Continued)

(58) Field of Classification Search
CPC . A61F 9/0008; A61K 9/0048; A61K 31/4178; A61P 27/10
See application file for complete search history.

(56) References Cited

U.S. PATENT DOCUMENTS 3,640,274 A  *  2/1972  Costello ................. A61H 35/02
                                                  128/200.14
3,779,245 A     12/1973  Windsor
(Continued)

FOREIGN PATENT DOCUMENTS

CN      103118642 A      5/2013
CN      104146816 A     11/2014
(Continued)

OTHER PUBLICATIONS

Merriam-Webster Definition of Collimated (Year: 2020).*
(Continued)

*Primary Examiner* — Benjamin J Klein
*Assistant Examiner* — Gabriella E Burnette
(74) *Attorney, Agent, or Firm* — Perilla Knox & Hildebrandt LLP; Stephanie L. Davy-Jow; Bradley K. Groff

(57) ABSTRACT

Methods of administering a liquid formulation of an ophthalmic agent to a topical ocular location of an eye are provided. Aspects of the methods include delivering to the topical ocular location a dose of the liquid formulation that can be wholly accommodated by the tear film of the eye. Devices and kits for practicing the methods are also provided. The methods, compositions and kits find use in a variety of applications, including therapeutic, diagnostic and cosmetic applications.

16 Claims, 22 Drawing Sheets

Related U.S. Application Data

(60) Provisional application No. 62/814,764, filed on Mar. 6, 2019, provisional application No. 62/656,552, filed on Apr. 12, 2018.

(51) Int. Cl.
| | |
|---|---|
| *A61K 31/135* | (2006.01) |
| *A61K 31/216* | (2006.01) |
| *A61K 31/4178* | (2006.01) |
| *A61K 31/4409* | (2006.01) |
| *A61K 31/46* | (2006.01) |
| *A61K 31/472* | (2006.01) |
| *A61K 31/573* | (2006.01) |
| *A61K 45/06* | (2006.01) |
| *A61K 47/34* | (2017.01) |
| *A61P 27/06* | (2006.01) |
| *A61P 27/10* | (2006.01) |

(52) U.S. Cl.
CPC ........ *A61K 31/216* (2013.01); *A61K 31/4178* (2013.01); *A61K 31/4409* (2013.01); *A61K 31/46* (2013.01); *A61K 31/472* (2013.01); *A61K 45/06* (2013.01); *A61P 27/06* (2018.01); *A61P 27/10* (2018.01); *A61K 31/573* (2013.01); *A61K 47/34* (2013.01)

(56) References Cited

U.S. PATENT DOCUMENTS

| | | | |
|---|---|---|---|
| 3,812,854 | A | 5/1974 | Michaels et al. |
| 3,861,386 | A | 1/1975 | Harris et al. |
| 3,934,585 | A * | 1/1976 | Maurice ................ A61F 9/0008 |
| | | | 604/298 |
| 3,970,250 | A | 7/1976 | Drews |
| 3,976,072 | A | 8/1976 | Walker |
| 4,159,803 | A | 7/1979 | Cameto et al. |
| 4,300,546 | A | 11/1981 | Kruber |
| 4,334,531 | A | 6/1982 | Reichl et al. |
| 4,338,576 | A | 7/1982 | Takahashi et al. |
| 4,344,744 | A | 8/1982 | Schuster et al. |
| 4,352,459 | A | 10/1982 | Berger et al. |
| 4,465,234 | A | 8/1984 | Maehara et al. |
| 4,632,311 | A | 12/1986 | Nakane et al. |
| 4,655,393 | A | 4/1987 | Berger |
| 4,793,339 | A | 12/1988 | Matsumoto et al. |
| 4,850,534 | A | 7/1989 | Takahashi et al. |
| 4,882,150 | A | 11/1989 | Kaufman |
| 4,952,581 | A | 8/1990 | Bito et al. |
| 4,961,345 | A | 10/1990 | Tsuruoka et al. |
| 4,976,259 | A | 12/1990 | Higson et al. |
| 4,981,625 | A | 1/1991 | Rhim et al. |
| 5,025,957 | A | 6/1991 | Ranalletta et al. |
| 5,171,306 | A | 12/1992 | Vo |
| 5,232,363 | A | 8/1993 | Meller |
| 5,368,582 | A | 11/1994 | Bertera |
| 5,370,317 | A | 12/1994 | Weston |
| 5,487,378 | A | 1/1996 | Robertson et al. |
| 5,549,249 | A | 8/1996 | Foster et al. |
| 5,624,057 | A | 4/1997 | Lifshey |
| 5,627,611 | A | 5/1997 | Scheiner |
| 5,630,793 | A | 5/1997 | Rowe |
| 5,657,926 | A | 8/1997 | Toda |
| 5,692,651 | A | 12/1997 | Fuchs |
| 5,811,443 | A | 9/1998 | DeSantis, Jr. et al. |
| 5,828,394 | A | 10/1998 | Khuri-Yakub et al. |
| 5,938,117 | A | 8/1999 | Ivri |
| 5,958,342 | A | 9/1999 | Gamble et al. |
| 5,960,224 | A | 9/1999 | Sanada et al. |
| 6,024,717 | A | 2/2000 | Ball et al. |
| 6,062,212 | A | 5/2000 | Davidson et al. |
| 6,065,623 | A | 5/2000 | Hierzer et al. |
| 6,095,376 | A | 8/2000 | Hennemann et al. |
| 6,196,218 | B1 | 3/2001 | Voges |
| 6,232,129 | B1 | 5/2001 | Wiktor |
| 6,273,092 | B1 | 8/2001 | Nolan |
| 6,302,101 | B1 | 10/2001 | Py |
| 6,467,476 | B1 | 10/2002 | Ivri et al. |
| RE38,077 | E | 4/2003 | Cohen et al. |
| 6,543,442 | B2 | 4/2003 | Gonda et al. |
| 6,629,646 | B1 | 10/2003 | Ivri |
| 6,730,066 | B1 | 5/2004 | Bennwik et al. |
| 6,758,837 | B2 | 7/2004 | Peclat et al. |
| 6,869,275 | B2 | 3/2005 | Dante et al. |
| 7,066,398 | B2 | 6/2006 | Borland et al. |
| 7,105,357 | B1 | 9/2006 | Kalkum et al. |
| 7,201,732 | B2 | 4/2007 | Anderson et al. |
| 7,314,938 | B2 | 1/2008 | Shen et al. |
| 7,571,722 | B2 | 8/2009 | Wuttke et al. |
| 7,745,460 | B2 | 6/2010 | Shen et al. |
| 7,790,743 | B2 | 9/2010 | Shen et al. |
| 7,874,467 | B2 | 1/2011 | Pardes et al. |
| 7,883,031 | B2 * | 2/2011 | Collins, Jr. .......... A61M 11/042 |
| | | | 239/338 |
| 7,928,122 | B2 | 4/2011 | Shen et al. |
| 8,012,136 | B2 | 9/2011 | Collins, Jr. et al. |
| 8,048,047 | B2 | 11/2011 | Domash |
| 8,056,766 | B2 | 11/2011 | Grevin |
| 8,128,606 | B2 | 3/2012 | Anderson et al. |
| 8,133,210 | B2 | 3/2012 | Al-Abdulla et al. |
| 8,144,399 | B2 | 3/2012 | Steenblik et al. |
| 8,168,655 | B2 | 5/2012 | Gadek et al. |
| 8,273,307 | B2 | 9/2012 | Eickhoff et al. |
| 8,367,701 | B2 | 2/2013 | Burnier et al. |
| 8,398,001 | B2 | 3/2013 | Borland et al. |
| 8,435,544 | B2 | 5/2013 | Mitra et al. |
| 8,544,462 | B2 | 10/2013 | Papania et al. |
| 8,545,463 | B2 | 10/2013 | Collins, Jr. et al. |
| 8,592,450 | B2 | 11/2013 | Gadek et al. |
| 8,629,111 | B2 | 1/2014 | Acheampong et al. |
| 8,633,162 | B2 | 1/2014 | Acheampong et al. |
| 8,642,556 | B2 | 2/2014 | Acheampong et al. |
| 8,648,048 | B2 | 2/2014 | Acheampong et al. |
| 8,684,980 | B2 * | 4/2014 | Hunter ................ B05B 17/0646 |
| | | | 604/296 |
| 8,685,930 | B2 | 4/2014 | Acheampong et al. |
| 8,722,728 | B2 | 5/2014 | Wong et al. |
| 8,733,935 | B2 | 5/2014 | Ballou, Jr. |
| 8,863,998 | B2 | 10/2014 | Painchaud et al. |
| 8,927,574 | B2 | 1/2015 | Burnier |
| 8,927,921 | B1 | 1/2015 | Nelms et al. |
| 8,936,021 | B2 | 1/2015 | Collins, Jr. |
| 9,039,666 | B2 | 5/2015 | Voss et al. |
| 9,068,566 | B2 | 6/2015 | Ivri |
| 9,085,553 | B2 | 7/2015 | Zeller et al. |
| 9,087,145 | B2 | 7/2015 | Ballou, Jr. et al. |
| 9,186,690 | B2 | 11/2015 | Scanlon et al. |
| 9,216,174 | B2 | 12/2015 | Shen et al. |
| 9,238,532 | B2 | 1/2016 | Decock et al. |
| 9,248,191 | B2 | 2/2016 | Acheampong et al. |
| 9,353,088 | B2 | 5/2016 | Burnier |
| 9,447,077 | B2 | 9/2016 | Burnier et al. |
| 9,597,230 | B2 | 3/2017 | Haffner et al. |
| 9,676,525 | B2 | 6/2017 | Greiner-Perth et al. |
| 9,700,686 | B2 | 7/2017 | Gavini et al. |
| 9,801,757 | B2 | 10/2017 | Voss et al. |
| 9,808,825 | B2 | 11/2017 | Aguilar et al. |
| 9,867,933 | B2 | 1/2018 | Pardes et al. |
| 9,890,141 | B2 | 2/2018 | Burnier |
| 10,073,949 | B2 | 9/2018 | Ballou, Jr. et al. |
| 10,105,720 | B2 | 10/2018 | Decock et al. |
| 10,124,000 | B2 | 11/2018 | Shen et al. |
| 10,154,923 | B2 | 12/2018 | Hunter et al. |
| 10,174,017 | B2 | 1/2019 | deLong et al. |
| 10,314,740 | B2 | 6/2019 | Kraft |
| 10,624,781 | B2 | 4/2020 | Ivri |
| 11,278,448 | B2 | 3/2022 | Palanker et al. |
| 2001/0035184 | A1 | 11/2001 | Schuler et al. |
| 2001/0036424 | A1 | 11/2001 | Takahashi et al. |
| 2001/0036449 | A1 | 11/2001 | Garst |
| 2002/0078947 | A1 | 6/2002 | Gumaste |
| 2002/0124843 | A1 | 9/2002 | Skiba et al. |
| 2002/0158196 | A1 | 10/2002 | Berggren et al. |

(56) References Cited

U.S. PATENT DOCUMENTS

| | | |
|---|---|---|
| 2002/0161344 A1 | 10/2002 | Peclat et al. |
| 2002/0185125 A1 | 12/2002 | Klimowicz et al. |
| 2002/0190079 A1 | 12/2002 | Hamamoto |
| 2003/0052573 A1 | 3/2003 | Wischnewskiy |
| 2003/0065294 A1 | 4/2003 | Pickup et al. |
| 2003/0071071 A1 | 4/2003 | Garcia et al. |
| 2003/0140921 A1 | 7/2003 | Smith et al. |
| 2004/0039355 A1 | 2/2004 | Gonzalez et al. |
| 2004/0050861 A1 | 3/2004 | Lisec et al. |
| 2004/0138630 A1 | 7/2004 | Al-Abdulla et al. |
| 2004/0163645 A1 | 8/2004 | Connelly et al. |
| 2004/0173642 A1 | 9/2004 | Clifford et al. |
| 2004/0204674 A1 | 10/2004 | Anderson et al. |
| 2004/0215157 A1 | 10/2004 | Peclat et al. |
| 2004/0256487 A1 | 12/2004 | Collins, Jr. et al. |
| 2004/0263567 A1 | 12/2004 | Hess et al. |
| 2005/0001981 A1 | 1/2005 | Anderson |
| 2005/0006417 A1 | 1/2005 | Nicol et al. |
| 2005/0107832 A1 | 5/2005 | Bernabei |
| 2005/0172962 A1 | 8/2005 | Gymaste et al. |
| 2005/0207917 A1 | 9/2005 | Koerner et al. |
| 2005/0240162 A1 | 10/2005 | Chen et al. |
| 2005/0261641 A1 | 11/2005 | Warchol et al. |
| 2006/0065677 A1 | 3/2006 | Py et al. |
| 2006/0069358 A1 | 3/2006 | Gerondale |
| 2006/0147313 A1 | 7/2006 | Zengerle et al. |
| 2006/0210604 A1 | 9/2006 | Dadey et al. |
| 2007/0051362 A1 | 3/2007 | Sullivan et al. |
| 2007/0088267 A1 | 4/2007 | Shekalim |
| 2007/0088268 A1 | 4/2007 | Edwards |
| 2007/0102455 A1 | 5/2007 | Stark et al. |
| 2007/0119969 A1 | 5/2007 | Collins et al. |
| 2007/0195151 A1 | 8/2007 | Anderson et al. |
| 2007/0268340 A1 | 11/2007 | Dacquay et al. |
| 2007/0295332 A1 | 12/2007 | Ziegler et al. |
| 2008/0039807 A1 | 2/2008 | Pine |
| 2008/0202514 A1 | 8/2008 | Kriksunov et al. |
| 2008/0214940 A1 | 9/2008 | Benaron et al. |
| 2008/0233053 A1 | 9/2008 | Gross et al. |
| 2008/0247264 A1 | 10/2008 | Gabl et al. |
| 2008/0257911 A1 | 10/2008 | Choi et al. |
| 2009/0060793 A1 | 3/2009 | Eickhoff et al. |
| 2009/0114742 A1 | 5/2009 | Collins, Jr. |
| 2009/0134235 A1 | 5/2009 | Ivri |
| 2009/0182291 A1 | 7/2009 | Eilat |
| 2009/0192443 A1 | 7/2009 | Collins, Jr. |
| 2009/0212127 A1 | 8/2009 | Reynolds et al. |
| 2009/0212133 A1 | 8/2009 | Collins, Jr. |
| 2009/0223513 A1 | 9/2009 | Papania et al. |
| 2010/0001090 A1 | 1/2010 | Neergaard et al. |
| 2010/0005903 A1 | 1/2010 | Beavis |
| 2010/0013352 A1 | 1/2010 | Pletner et al. |
| 2010/0044460 A1 | 2/2010 | Sauzade |
| 2010/0072302 A1* | 3/2010 | Cater ................. B05B 1/3053 239/333 |
| 2010/0076388 A1 | 3/2010 | Cater |
| 2010/0147899 A1 | 6/2010 | Nardi |
| 2010/0186738 A1 | 7/2010 | Kobayashi et al. |
| 2010/0222752 A1 | 9/2010 | Collins, Jr. et al. |
| 2010/0236545 A1 | 9/2010 | Kern |
| 2010/0295420 A1 | 11/2010 | Wierach |
| 2010/0326431 A1 | 12/2010 | Yu |
| 2011/0074247 A1 | 3/2011 | Hohlfeld et al. |
| 2011/0102735 A1 | 5/2011 | Gupta et al. |
| 2011/0106025 A1 | 5/2011 | Hall et al. |
| 2011/0146670 A1 | 6/2011 | Gallem et al. |
| 2011/0284579 A1 | 11/2011 | Pardes et al. |
| 2011/0293452 A1 | 12/2011 | Kim et al. |
| 2011/0305425 A1 | 12/2011 | Fabrykowski et al. |
| 2012/0017898 A1 | 1/2012 | Moller |
| 2012/0062840 A1 | 3/2012 | Ballou, Jr. et al. |
| 2012/0070467 A1 | 3/2012 | Ballou, Jr. et al. |
| 2012/0143152 A1 | 6/2012 | Hunter et al. |
| 2012/0179122 A1 | 7/2012 | Eilat et al. |
| 2012/0197219 A1 | 8/2012 | Scanlon et al. |
| 2012/0304929 A1 | 12/2012 | Ivri |
| 2013/0002095 A1 | 1/2013 | Van der Linden |
| 2013/0017283 A1 | 1/2013 | Zemel et al. |
| 2013/0025038 A1 | 1/2013 | Frey |
| 2013/0053042 A1 | 2/2013 | Tanikawa et al. |
| 2013/0079733 A1 | 3/2013 | Burt et al. |
| 2013/0118619 A1 | 5/2013 | Loth et al. |
| 2013/0140225 A1 | 6/2013 | Decock et al. |
| 2013/0150812 A1 | 6/2013 | Hunter et al. |
| 2013/0152796 A1 | 6/2013 | Pawl |
| 2013/0153677 A1 | 6/2013 | Leen et al. |
| 2013/0164436 A1 | 6/2013 | Yagi et al. |
| 2013/0172830 A1 | 7/2013 | Hunter et al. |
| 2013/0206857 A1 | 8/2013 | Ivri |
| 2013/0299607 A1 | 11/2013 | Wilkerson et al. |
| 2013/0345672 A1 | 12/2013 | Ferreri et al. |
| 2014/0088524 A1 | 3/2014 | Marx |
| 2014/0113946 A1* | 4/2014 | Abad ................. A61K 31/5415 514/397 |
| 2014/0157956 A1 | 6/2014 | Date et al. |
| 2014/0171490 A1 | 6/2014 | Gross et al. |
| 2014/0187969 A1 | 7/2014 | Hunter et al. |
| 2014/0214024 A1 | 7/2014 | Eichler |
| 2014/0224267 A1 | 8/2014 | Levits et al. |
| 2014/0242022 A1 | 8/2014 | Vehige et al. |
| 2014/0249491 A1 | 9/2014 | Ballou, Jr. et al. |
| 2014/0257172 A1 | 9/2014 | Yalamanchili |
| 2014/0274910 A1 | 9/2014 | Cumberlidge et al. |
| 2014/0276054 A1 | 9/2014 | Hossack et al. |
| 2014/0285121 A1 | 9/2014 | Balogh et al. |
| 2014/0323931 A1 | 10/2014 | Avni |
| 2014/0336596 A1 | 11/2014 | Wochele |
| 2014/0336618 A1 | 11/2014 | Wilkerson et al. |
| 2015/0018781 A1 | 1/2015 | Rindeknect et al. |
| 2015/0035180 A1 | 2/2015 | Shen et al. |
| 2015/0036219 A1 | 2/2015 | Shen et al. |
| 2015/0040891 A1 | 2/2015 | Avni |
| 2015/0086397 A1 | 3/2015 | Ma |
| 2015/0097050 A1 | 4/2015 | Ciervo |
| 2015/0139973 A1 | 5/2015 | Steinfeld et al. |
| 2015/0144128 A1 | 5/2015 | Hijlkema et al. |
| 2015/0209174 A1 | 7/2015 | Abreu |
| 2015/0209178 A1 | 7/2015 | Blakey et al. |
| 2015/0238689 A1 | 8/2015 | Shimizu |
| 2015/0256730 A1 | 9/2015 | Shen et al. |
| 2015/0276994 A1 | 10/2015 | Shen et al. |
| 2015/0308421 A1 | 10/2015 | Vogt |
| 2015/0328151 A1 | 11/2015 | Ballou, Jr. et al. |
| 2015/0352297 A1 | 12/2015 | Stedman et al. |
| 2016/0107180 A1 | 4/2016 | Decock et al. |
| 2016/0120833 A1 | 5/2016 | Wan et al. |
| 2016/0129467 A1 | 5/2016 | Ciardella et al. |
| 2016/0199225 A1 | 7/2016 | Ivri |
| 2016/0199230 A1 | 7/2016 | Doshi et al. |
| 2016/0213866 A1 | 7/2016 | Tan |
| 2016/0263314 A1 | 9/2016 | Pardes et al. |
| 2016/0296367 A1* | 10/2016 | Ivri ................. A61F 9/0008 |
| 2016/0354559 A1 | 12/2016 | Gavini et al. |
| 2017/0028626 A1 | 2/2017 | Delrot et al. |
| 2017/0136484 A1 | 5/2017 | Wilkerson et al. |
| 2017/0138357 A1 | 5/2017 | Kondo et al. |
| 2017/0151088 A1 | 6/2017 | Ballou, Jr. et al. |
| 2017/0156927 A1 | 6/2017 | Richter et al. |
| 2017/0182510 A1 | 6/2017 | Wilkerson et al. |
| 2017/0187969 A1 | 6/2017 | Kitamori et al. |
| 2017/0274159 A1 | 9/2017 | Gavini et al. |
| 2017/0344714 A1 | 11/2017 | Ballou, Jr. |
| 2018/0085251 A1 | 3/2018 | Hunter et al. |
| 2018/0116871 A1 | 5/2018 | Hunter et al. |
| 2018/0207030 A1 | 7/2018 | Ivri et al. |
| 2018/0229247 A1 | 8/2018 | Laidler |
| 2018/0236466 A1 | 8/2018 | Laidler |
| 2018/0297053 A1 | 10/2018 | Buckland et al. |
| 2019/0053945 A1 | 2/2019 | Hunter et al. |
| 2019/0074086 A1 | 3/2019 | Ballou, Jr. et al. |
| 2019/0099071 A1 | 4/2019 | Ehrmann |
| 2019/0314195 A1 | 10/2019 | Ivri et al. |
| 2019/0314196 A1 | 10/2019 | Ivri et al. |
| 2019/0314197 A1 | 10/2019 | Ivri et al. |

(56) References Cited

U.S. PATENT DOCUMENTS

| | | |
|---|---|---|
| 2019/0314198 A1 | 10/2019 | Ivri et al. |
| 2020/0022416 A1 | 1/2020 | Alarcon |
| 2020/0197218 A1 | 6/2020 | Newell et al. |
| 2020/0197220 A1 | 6/2020 | Ivri |
| 2020/0246182 A1 | 8/2020 | Ivri |
| 2020/0281768 A1 | 9/2020 | Quintana et al. |
| 2020/0315842 A1 | 10/2020 | Palanker et al. |
| 2020/0330267 A1 | 10/2020 | Li et al. |
| 2021/0128350 A1 | 5/2021 | Ivri |
| 2021/0137732 A1 | 5/2021 | Quintana |
| 2021/0220169 A1 | 7/2021 | Ivri |
| 2021/0322209 A1 | 10/2021 | Ivri |
| 2021/0322210 A1 | 10/2021 | Ivri |
| 2022/0039998 A1 | 2/2022 | Ivri |
| 2022/0125631 A1 | 4/2022 | Tanchulev et al. |
| 2022/0160542 A1 | 5/2022 | Palanker |
| 2022/0192874 A1 | 6/2022 | Ivri |

FOREIGN PATENT DOCUMENTS

| | | |
|---|---|---|
| CN | 104582647 A | 4/2015 |
| CN | 204813955 U | 12/2015 |
| CN | 105351426 A | 2/2016 |
| CN | 107530509 A | 1/2018 |
| EP | 0622035 A1 | 11/1994 |
| EP | 0622035 B1 | 3/1999 |
| EP | 1493410 A2 | 1/2005 |
| JP | H08251948 A | 9/1996 |
| JP | 3055480 U | 1/1999 |
| JP | 2007531577 A | 11/2007 |
| JP | 2013535250 A | 9/2013 |
| KR | 10-1258025 B1 | 4/2013 |
| KR | 10-2013-0054352 A | 5/2013 |
| WO | 1994020875 A3 | 1/1995 |
| WO | 1996000050 A1 | 1/1996 |
| WO | 2000005482 A1 | 2/2000 |
| WO | WO2001046134 A1 | 6/2001 |
| WO | 2002072169 A2 | 9/2002 |
| WO | 2010078428 A1 | 7/2010 |
| WO | 2012009706 A1 | 1/2012 |
| WO | 2013076682 A1 | 5/2013 |
| WO | WO2013090459 A1 | 6/2013 |
| WO | WO2013090468 A1 | 6/2013 |
| WO | WO2013155201 A2 | 10/2013 |
| WO | WO2013158967 A1 | 10/2013 |
| WO | WO2013158967 A2 | 10/2013 |
| WO | WO2016115050 A1 | 7/2016 |
| WO | WO2016164830 A1 | 10/2016 |
| WO | 2018136618 A2 | 7/2018 |
| WO | 2018227190 A1 | 12/2018 |
| WO | 2019113483 A1 | 6/2019 |
| WO | 2020010116 A1 | 1/2020 |

OTHER PUBLICATIONS

Kent, Christopher, "Getting Meds onto the Eye, 21st Century Style", Review of Ophthalmology Mar. 15, 2013 (Year: 2013).*

Ianchulev et al., "Pharmacodynamic profile of mydriatic agents delivered by ocular piezo-ejection microdosing compared with conventional eyedropper", 2016, Ther. Deliv. 7(11), 751-760 (Year: 2016).*

"Spherical mirrors" The Physics Hypertextbook <https://physics.info/mirrors/>. (Year: 2021).*

Electronic Tutorials: Linear Solenoid Actuator <https://www.electronics-tutorials.ws/io/io_6.html>. (Year: 2016).*

Gannon, Megan "The best length for eye lashes" Live Science, Feb. 24, 2015, <https://www.livescience.com/49934-optimal-length-for-eyelashes-discovered.html>. (Year: 2015).*

Choi et al., Generation of Controllable Monodispersed Sprays Using Impulse Jet and Charging Techniques, Review of Scientific Instruments, Jun. 1990, vol. 61, No. 6, p. 1689-1693.

Jow, Design and Optimization of Printed Spiral Coils for Efficient Transcutaneous Inductive Power Transmission, IEEE Transactions on Biomedical Circuits and Systems, Sep. 2007, vol. 1, No. 3, p. 193-202.

Lindblad et al., Production of Uniform-Sized Liquid Droplets, Journal of Scientific Instruments, 1965, vol. 42, No. 8, p. 635-638.

Murube et al., Classification of Artificial Tears, I: Composition and Properties, Advanced Experimental Medical Biology, 438:693-704, 49, 1998a.

Murube et al., Classification of Artificial Tears, II: Additives and Commercial Formulas, Advanced Experimental Medical Biology, 438:705-715, 1998b.

Macmillan Online Dictionary entry for "Stream," https://macmillandictionary.com/dictionary/american/stream_1#stream_9, Accessed Thu Dec. 13, 2018.

Oxford Online Dictionary entry for "Stream," https://en.oxforddictionaries.com/definition/us/stream, Accessed Thu Dec. 13, 2018.

Vocabulary.com Online Dictionary entry for "Stream," https://www.dictionary.com/stream, Accessed Thu Dec. 13, 2018.

Abidie et al., Lifitegrast: A Novel Drug for Treatment of Dry Eye Disease, Journal of Pharmacology and Pharmacotherapy, Oct.-Dec. 2016, vol. 7, No. 4, p. 194-198.

Ali et al., Glaucoma and Dry Eye, Ophthalmology, Jun. 2009, vol. 116, No. 6, p. 1232.

Kent, Getting Meds onto the Eye, 21st Century Style, Review of Ophthalmology, Mar. 15, 2013, https://www.reviewofophthalmology.com/article/getting-meds-onto-the-eye-21st-century-style, p. 1-6, accessed Aug. 27, 2019.

Lallemand et al., Cyclosporine A Delivery to the Eye: A Comprehensive Review of Academic and Industrial Efforts, European Journal of Pharmaceutics and Biopharmaceutics, Aug. 2017, vol. 117, p. 14-28.

Lux et al., A comparative bioavailability study of three conventional eye drops versus a single lyophilisate, Br J Ophthalmol. Apr. 2003;87(4):436-40.

Jow et al., Design and Optimization of Printed Spiral Coils for Efficient TranscutaneousInductive Power Transmission, IEEE Transactions on Biomedical Circuits and Systems, vol. 1, No. 3, Sep. 2007.

Murube et al., 99 Classification of Artificial Tears, Composition and Properties, Dept. of Ophthalmology, Madrid, Spain, pp. 693-704.

Murube et al., 100 Classification of Artificial Tears, Additives and Commercial Formulas, Dept. of Ophthalmology, Madrid, Spain, p. 705.

Choi et al., Generation of controllable monodispersed sprays using impulse jet and charging techniques, Review of Ccientific Instruments 61, 1689 (1990).

Lindblad et al., Production of uniform-sized liquid droplets, Journal of Scientific Instruments, vol. 42, No. 8, 1965.

Ianchulev et al., "Pharmacodynamic profile of mydriatic agents delivered by ocular piezo-ejection microdosing compared with conventional eyedropper", 2016, Ther. Deliv. 7(11), 751-760.

Choi et al., "Generation of controllable monodispersed sprays using impulse jet and charging techniques", 1990, Review of Scientific Instruments 61, 1689.

Birkhoff et al., "New Devices for Dispensing Ophthalmic Treatments May Be the Key to Managing the Life Cycles of Established Products", 2010, Drug Delivery Technology, vol. 10, pp. 16-21.

Brenton, "CRUK/10/30: TRICON8⇒Sample collection of ovarian cancer tissues and blood for translational research from patients participating in the CR-UK/MRC ICON8 trial", 2015, online abstract.

Denion et al., "A 5-Minute Interval between Two Dilating Eye Drops Increases Their Effect", Jul. 19, 2017, Optometry and Vision Science, vol. 94, pp. 838-844.

Kompella et al., "ISOPT Clinical Hot Topic Panel Discussion on Ocular Drug Delivery", 2019, J. Ocul. Pharmacol. Ther., vol. 35, pp. 457-465.

Marx et al., "Opthalmic Squeeze Dispenser: Eliminating the Need for Additives in Multidose Preservative-Free Eyecare Formulations", 2017, Drug Development Delivery, vol. 17, pp. 40-44.

Merriam-Webster, "Clamp," 2019 [online]; [Retrieved on Oct. 25, 2022], Retrieved from the Internet URL: https://www.merriam-webster.com/dictionary/clamp.

(56) References Cited

OTHER PUBLICATIONS

Merriam-Webster, "Collimate," 2020 [online]; [Retrieved on Oct. 17, 2022], Retrieved from the Internet URL: https://www.merriam-webster.com/dictionary/collimated.

Merriam-Webster, "Stream," n.d. [online]; [Retrieved on Dec. 13, 2018], Retrieved from the Internet URL: https://www.merriam-webster.com/dictionary/stream.

Pronin et al., "Teaching an Old Drug New Tricks: Agonism, Antagonism, and Biased Signaling of Pilocarpine through M3 Muscarinic Acetylcholine Receptor", 2017, Mol. Pharmacol., vol. 92, pp. 601-612.

International Search Report and Written Opinion dated Jul. 1, 2019 in corresponding International Patent Application No. PCT/US2019/027018 (7 pages).

* cited by examiner

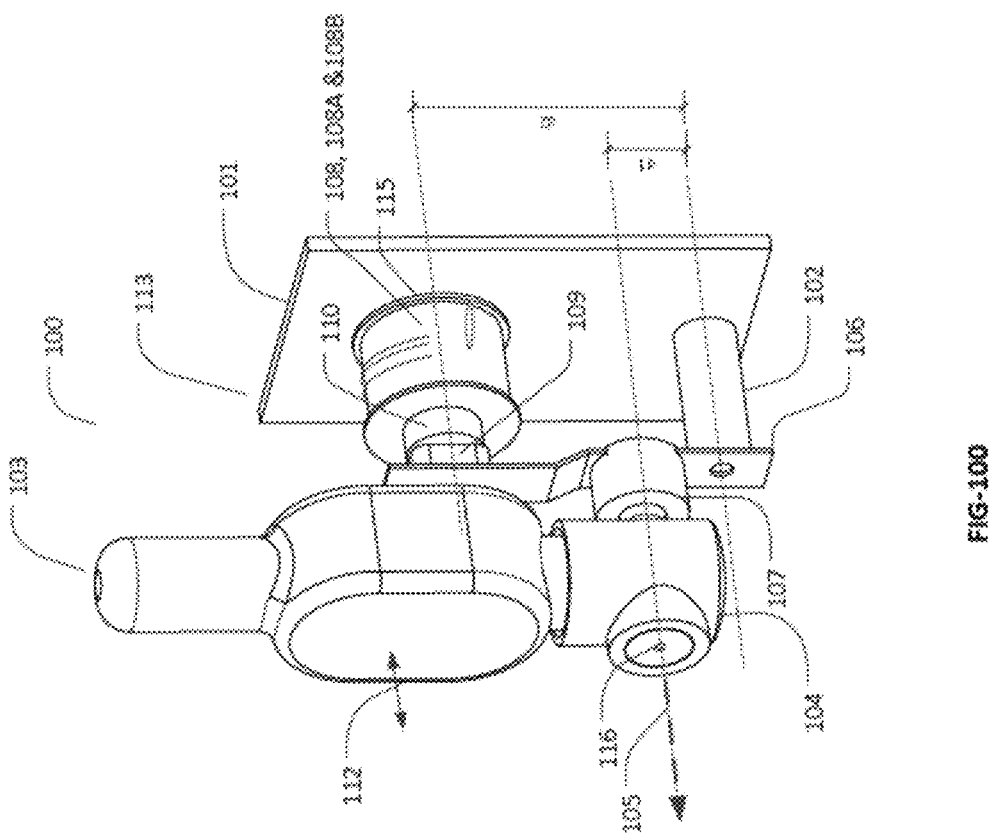

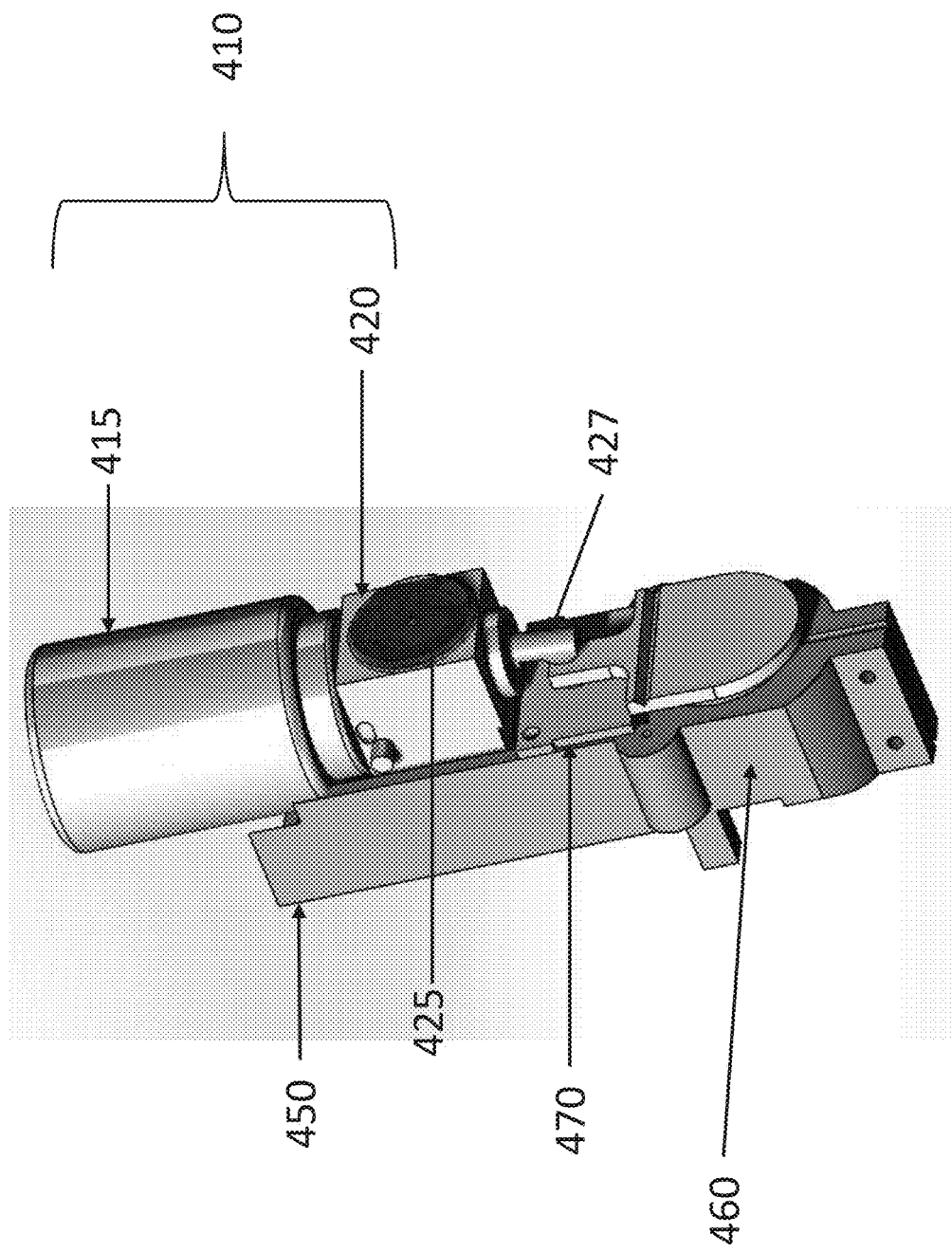

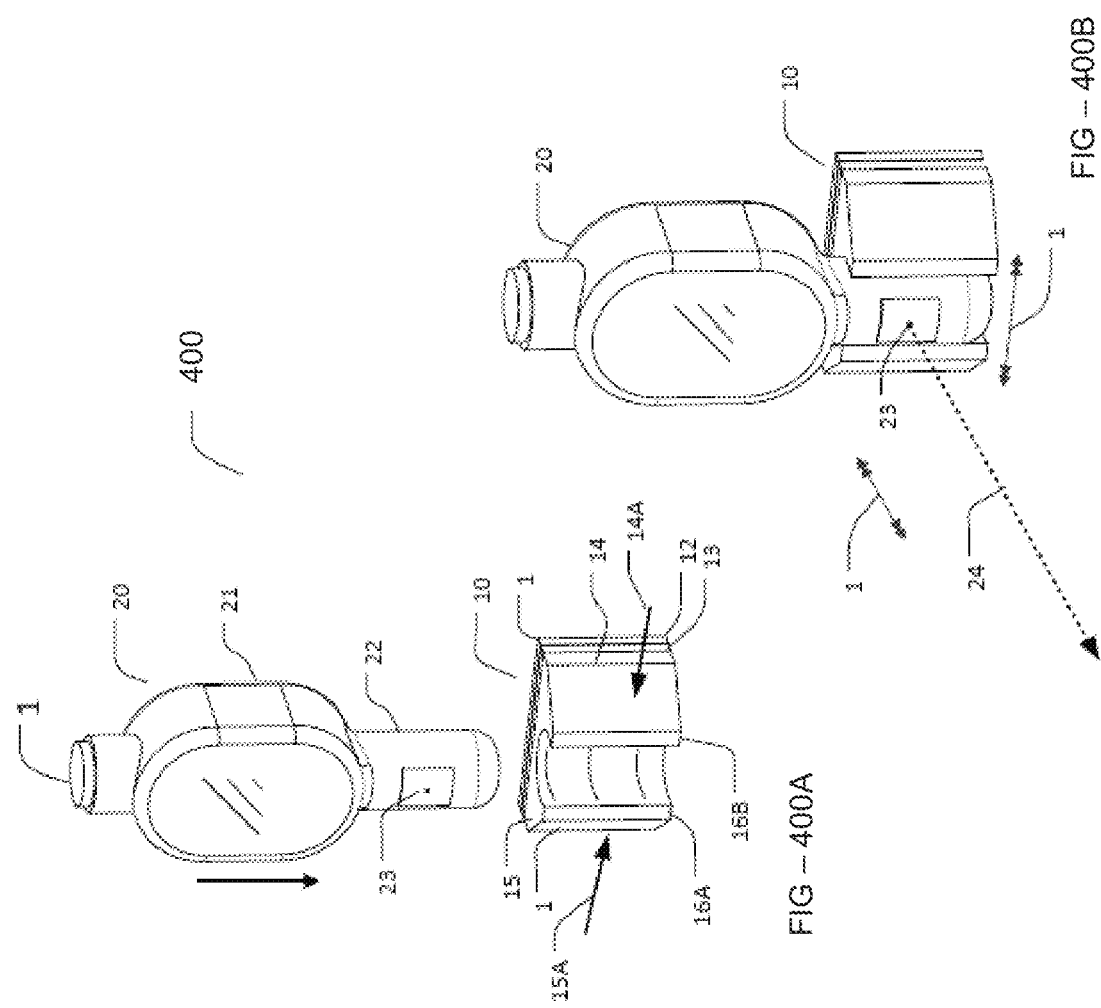

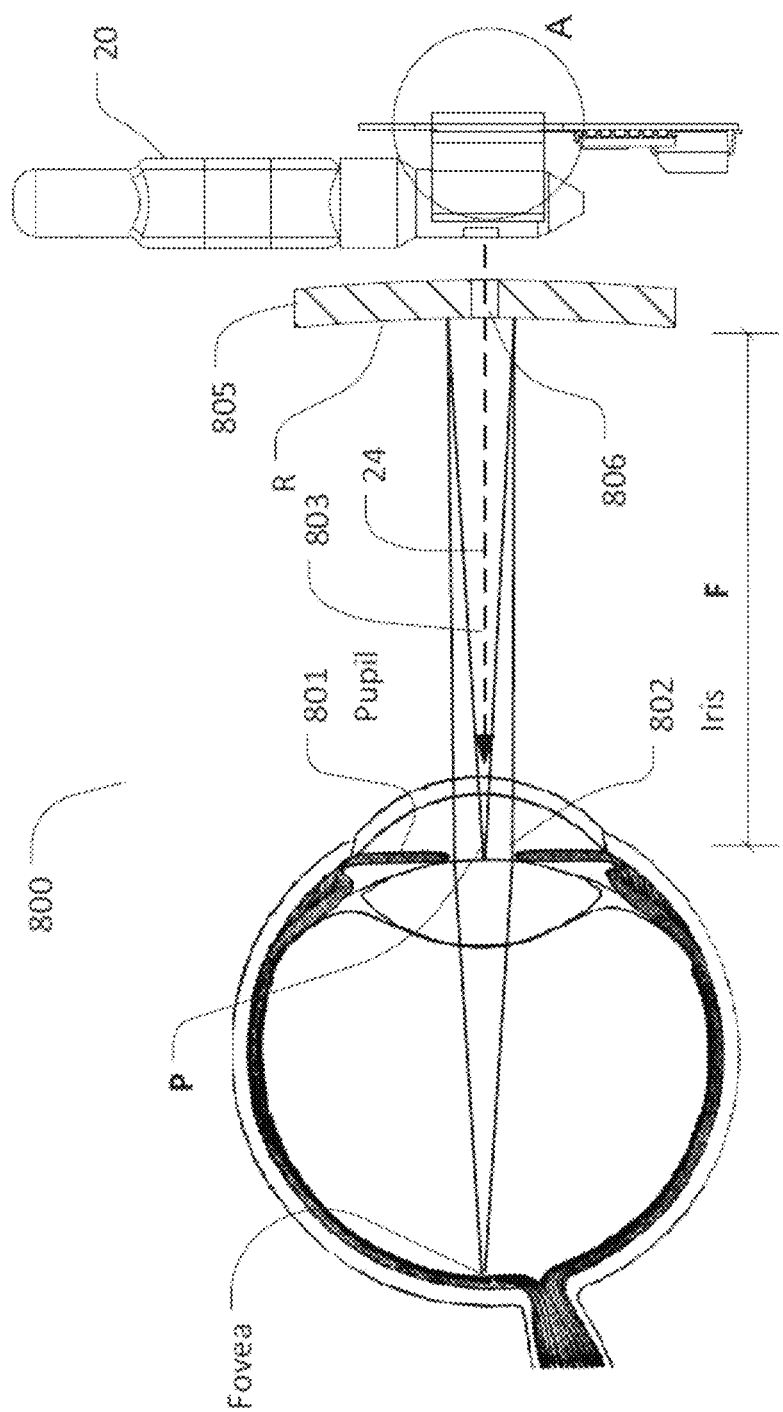

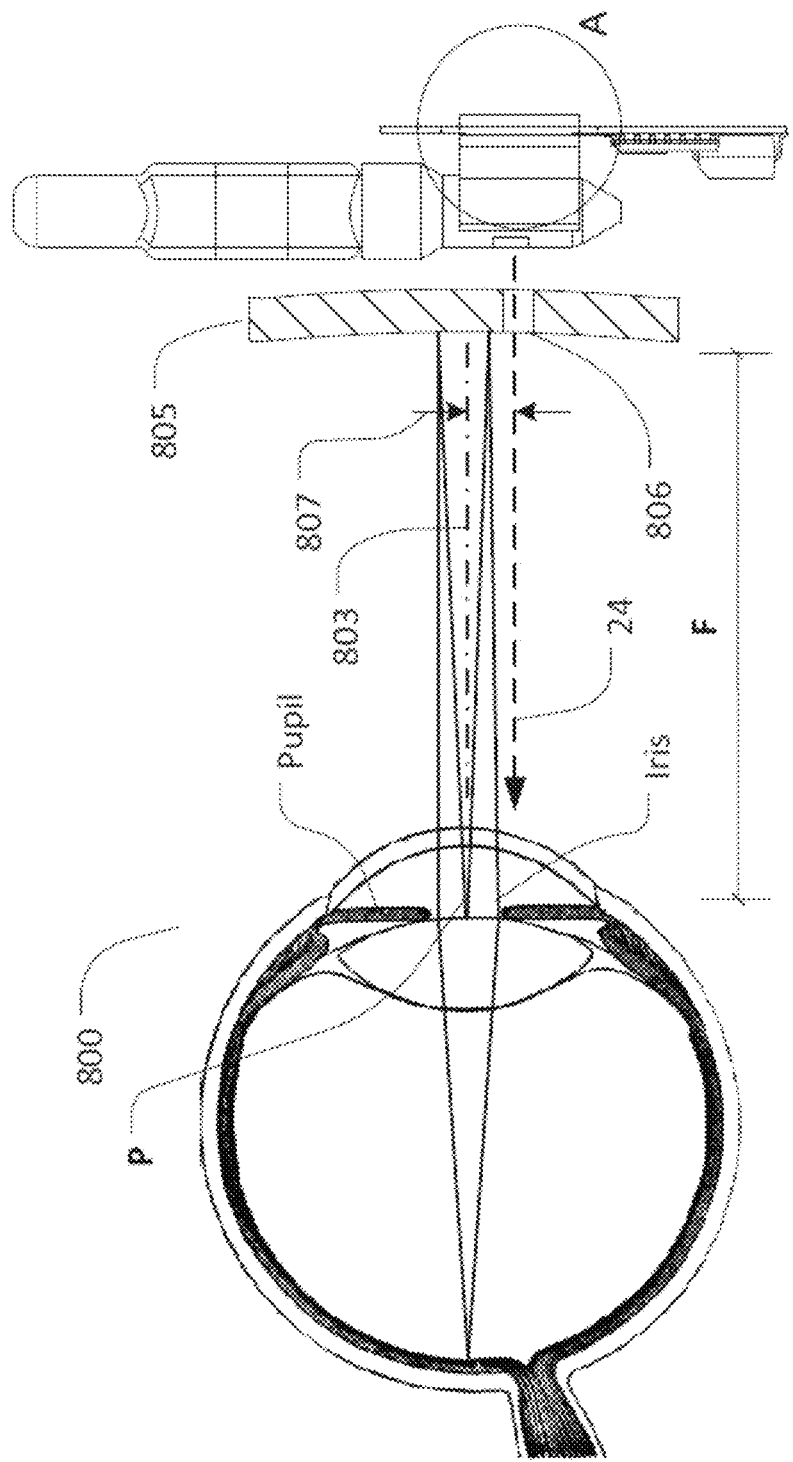

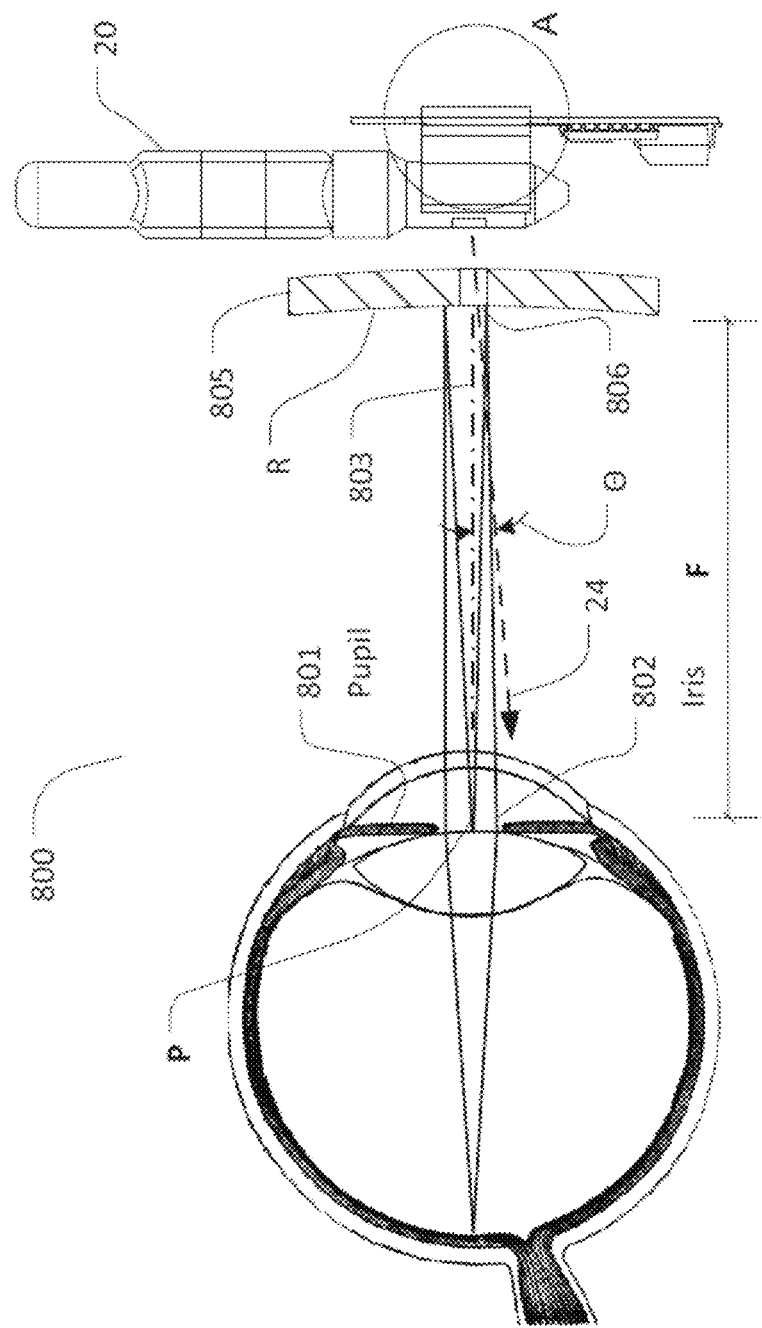

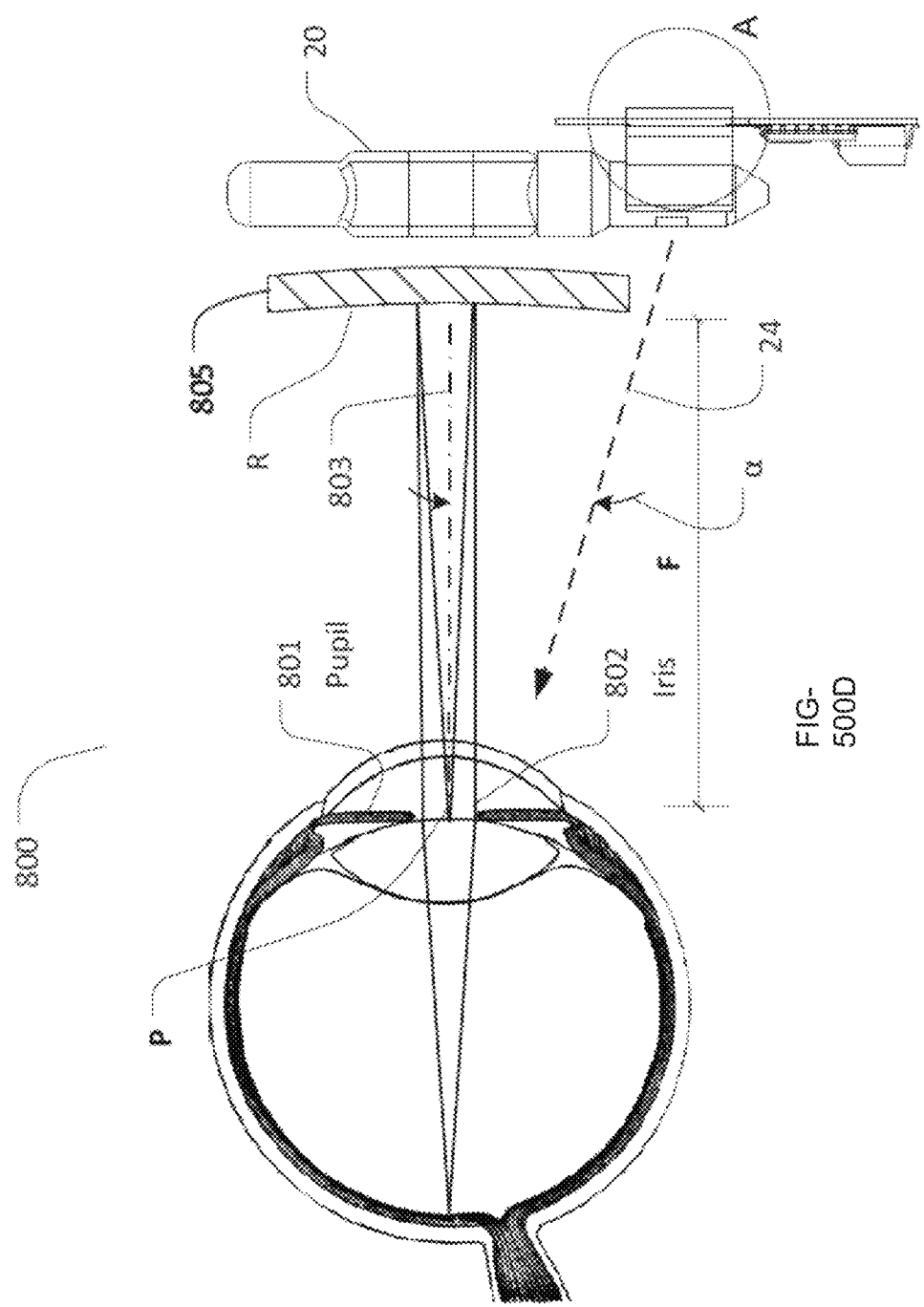

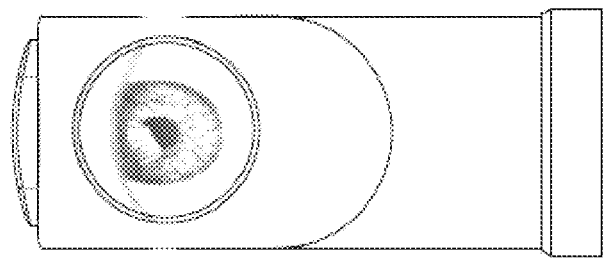
FIG-600C
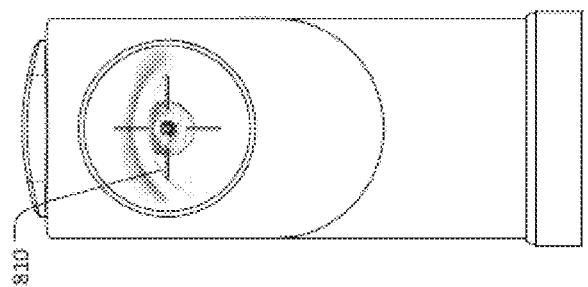
FIG-600B
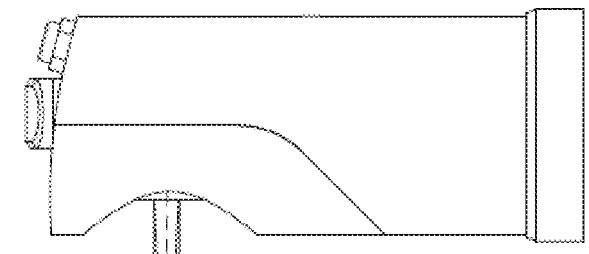
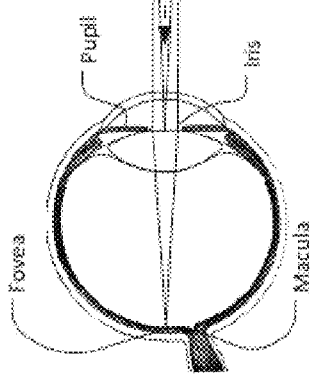
FIG-600A

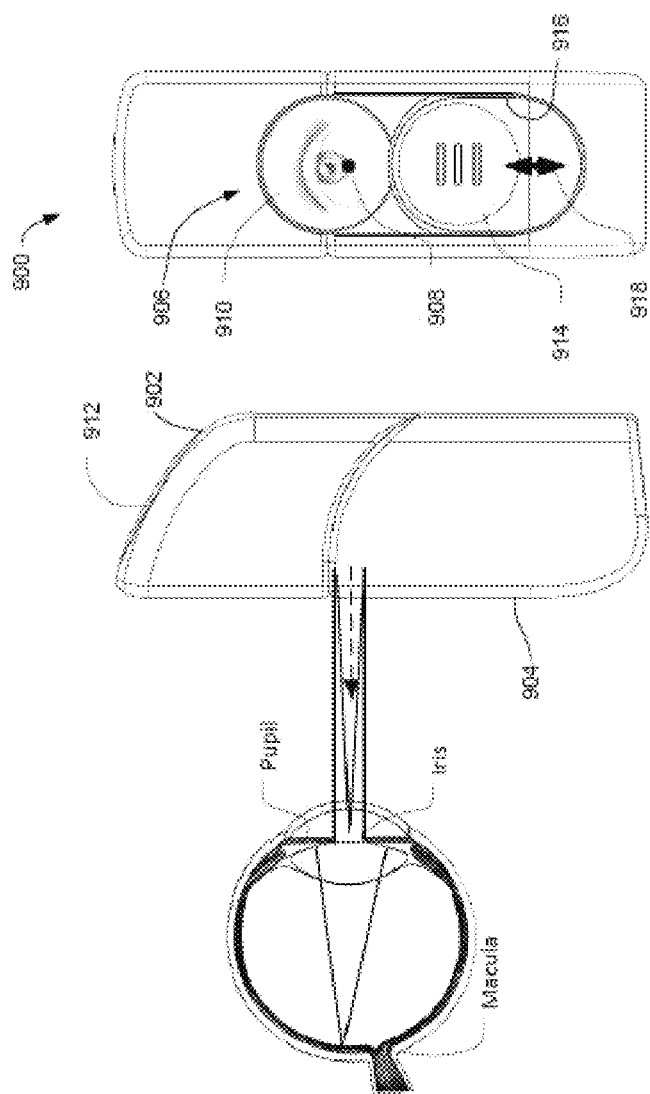

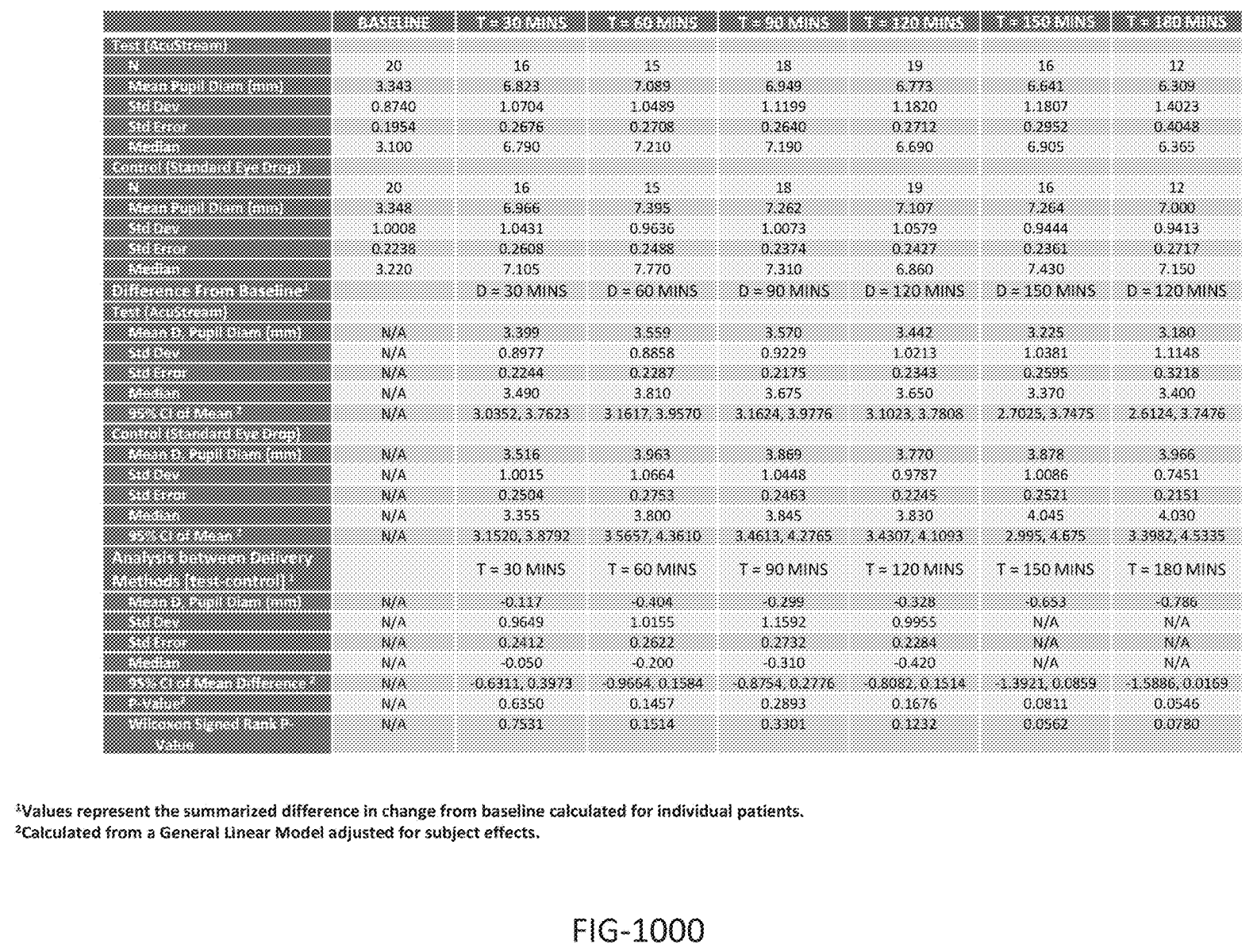

FIG-1000

¹Values represent the summarized difference in change from baseline calculated for individual patients.
²Calculated from a General Linear Model adjusted for subject effects.

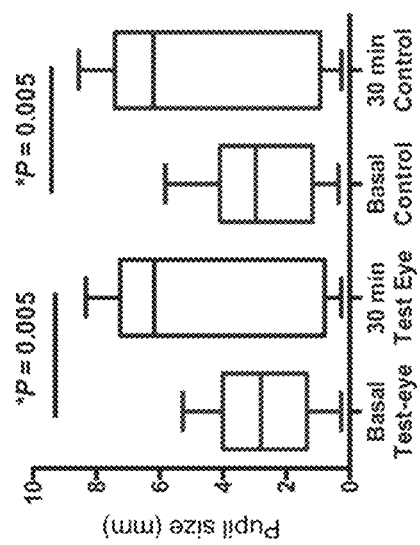
FIG-1100

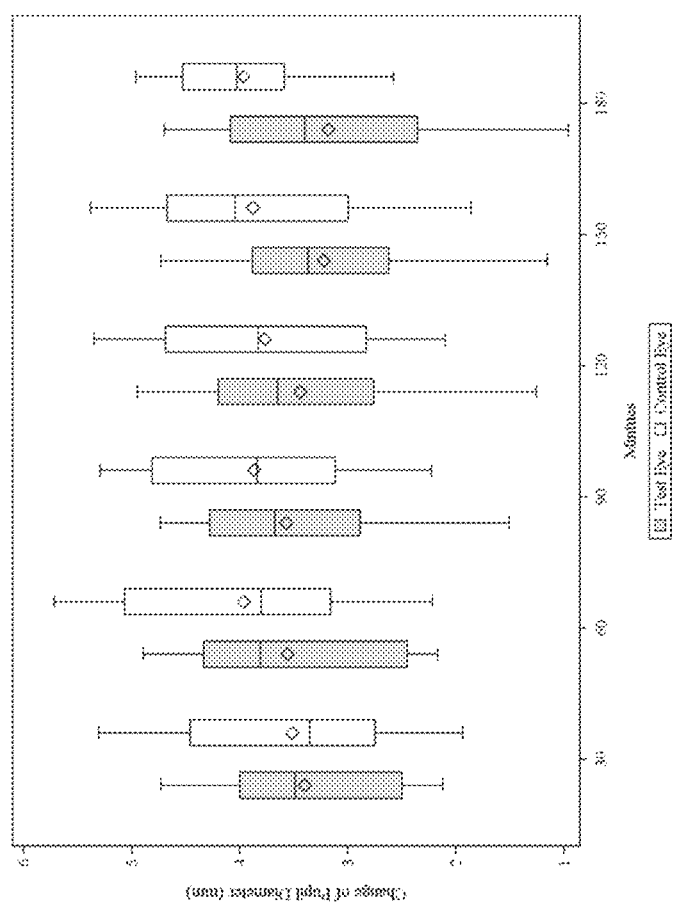
FIG-1200

| | TEST (ACULEAR) | | CONTROL (STANDARD OF CARE) | |
|---|---|---|---|---|
| | PRE-TEST (BASELINE) | POST-TEST | PRE-TEST (BASELINE) | POST-TEST |
| RIGHT EYE (OD) | | | | |
| N | 9 | 9 | 9 | 9 |
| Mean Pressure (mmHg) | 18.7 | 13.7 | 17.2 | 13.3 |
| Std Dev | 2.83 | 3.32 | 2.95 | 4.03 |
| Std Err | 0.94 | 1.11 | 0.98 | 1.34 |
| Median | 18.0 | 13.0 | 18.0 | 12.0 |
| Min, Max | 15, 24 | 10, 20 | 12, 21 | 10, 22 |
| LEFT EYE (OS) | | | | |
| N | 9 | 9 | 9 | 9 |
| Mean Pressure (mmHg) | 18.4 | 13.4 | 18.1 | 13.3 |
| Std Dev | 2.74 | 2.70 | 5.18 | 4.09 |
| Std Err | 0.91 | 0.90 | 1.73 | 1.36 |
| Median | 18.0 | 13.0 | 18.0 | 12.0 |
| Min, Max | 15, 24 | 11, 20 | 12, 30 | 10, 22 |
| BOTH EYES (OU) | | | | |
| N | 18 | 18 | 18 | 18 |
| Mean Pressure (mmHg) | 18.6 | 13.6 | 17.7 | 13.3 |
| Std Dev | 2.71 | 2.94 | 4.12 | 3.94 |
| Std Err | 0.64 | 0.69 | 0.97 | 0.93 |
| Median | 18.0 | 13.0 | 18.0 | 12.0 |
| Min, Max | 15, 24 | 11, 20 | 12, 30 | 10, 22 |
| Analysis of Change from Baseline | | | | |
| Mean Pressure Change (mmHg) | | -5.0 | | -4.3 |
| Std Dev | | 1.75 | | 3.25 |
| Std Err | | 0.41 | | 0.77 |
| Median | | -5.0 | | -4.0 |
| Min, Max | | -8, -2 | | -12, 2 |
| 95% CI Mean Difference | | -6.25, -3.75 | | -5.58, -3.08 |
| Statistical Analysis Between Delivery | | | | |
| Methods (Test-Control) | | | | |
| Mean Pressure Change Difference | | -0.7 | | |
| 95% CI of Mean Difference | | -2.44, 1.10 | | |
| p-Value | | 0.4492 | | |
| Wilcoxon Rank Sum p-Value | | 0.3447 | | |

FIG-1300

[1]Values represent the summarized difference in change from baseline calculated for individual patients.

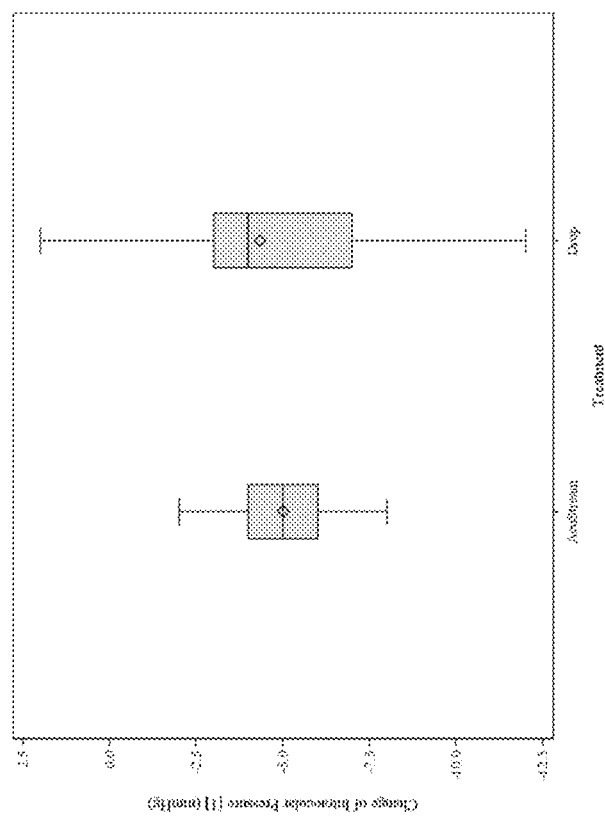
FIG-1400

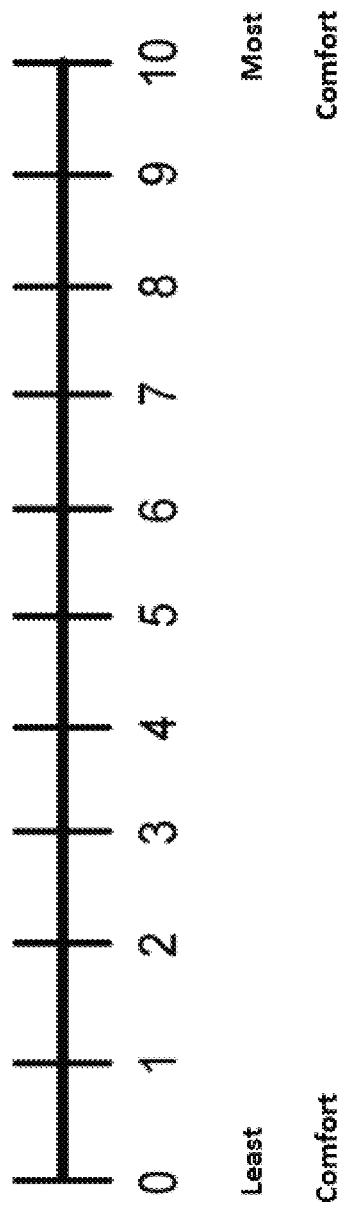

TOPICAL OCULAR DELIVERY METHODS AND DEVICES FOR USE IN THE SAME

CROSS-REFERENCE TO RELATED APPLICATIONS

This application is a continuation-in-part of PCT Application Serial No. US2019/027018 filed Apr. 11, 2019, which application, pursuant to 35 U.S.C. § 119 (e), claims priority to the filing date of U.S. Provisional Patent Application Ser. No. 62/656,552 filed Apr. 12, 2018, and U.S. Provisional Patent Application Ser. No. 62/814,764 filed Mar. 6, 2019; the disclosures of which applications are herein incorporated by reference.

INTRODUCTION

There are many situations in which it is desirable to administer a liquid formulation to an ocular surface, e.g., for the treatment of an ocular condition, such as a disease condition, for the alleviation of discomfort, e.g., dry eye, for the improvement of appearance, e.g., bloodshot eye, and for diagnostic purposes. The administration of liquid formulations onto an ocular surface generally is accomplished by depositing one or more drops of the liquid formulation from a small container or bottle (e.g., a conventional eye dropper) directly onto the ocular surface. In such instances, the drops of the liquid formulation are either self-administered or administered by another, such as a health care provider or caregiver.

A conventional eye dropper dispenses single drops that are about 30-50 µl in volume. However, since the human eye can typically retain only about 7 µl of fluid on the corneal surface, larger deposited volumes result in overflow and loss of most of the medication from the eye surface. In addition, a large volume of a single drop, such as 30 or 50 µl, causes a blinking reflex, which removes the majority of the fluid from the ocular surface, and also causes discomfort and reflex tearing.

These factors can make administration of eye drops from conventional eye droppers (whether self-administered or administered by another) problematic. For example, with conventional eye droppers it is not possible to administer a precise, known dose of a liquid formulation and active agent to the eye. Furthermore, there is substantial waste that occurs using conventional eye droppers. In addition, administration by conventional eye dropper can result in patient discomfort.

SUMMARY

Embodiments of the invention address the need in the art for improved administration of liquid formulations to the ocular surface. Improvements realized by embodiments of the invention include, but are not limited to: the ability to administer a precise, known dose of a liquid formulation and active agent to the eye; the elimination of liquid formulation waste and the reduction, if not elimination, of patient discomfort during ocular administration.

Methods of administering a liquid formulation of an ophthalmic agent to a topical ocular location of an eye are provided. Aspects of the methods include delivering to the topical ocular location a dose of the liquid formulation that can be wholly accommodated by the tear film of the eye. Devices and kits for practicing the methods are also provided. The methods, compositions and kits find use in a variety of applications, including therapeutic, diagnostic and cosmetic applications.

BRIEF DESCRIPTION OF THE FIGURES

Having thus summarized the general nature of the invention and some of its features and advantages, certain embodiments and modifications thereof will become apparent to those skilled in the art from the detailed description herein having reference to the figures that follow, of which:

FIG. 100 illustrates a perspective view of an embodiment of the invention.

FIG. 300B, FIG. 300C and FIG. 300D illustrate various views of such a device that includes a cover to seal the orifice and allow for use of a preservative free liquid formulation.

FIG. 400A and FIG. 400B provide views of an internal mechanism of a handheld device that includes a piezoelectric actuator according to an embodiment of the invention;

FIG. 500A illustrates an alignment system which facilitates aligning the fluid delivery assembly relative to the eye of the user when a reflected image of the eye appears in focus to the user. FIG. 500B, FIG. 500C and FIG. 500D illustrate variations where the fluid is emitted off-axis or at an angle relative to a central visual axis of the iris.

FIG. 600A, FIG. 600B and FIG. 600C illustrate side and front views of the assembly when the eye of the user is properly positioned relative to the assembly for fluid delivery. FIG. 600C illustrates a front view of the assembly where the radius of curvature of the mirror is relatively smaller than in FIG. 600B such that the image of an eye in reflection appears at higher magnification than in FIG. 600B.

FIG. 700A and FIG. 700B illustrate front and side views of an embodiment of the assembly having a protective covering feature.

FIGS. 900A to 1400 provide further details regarding results obtained during experiments as described in the Experimental section, below.

FIG. 1500 provides a patient Analog Visual Comfort Scale.

DETAILED DESCRIPTION

Figure 200:
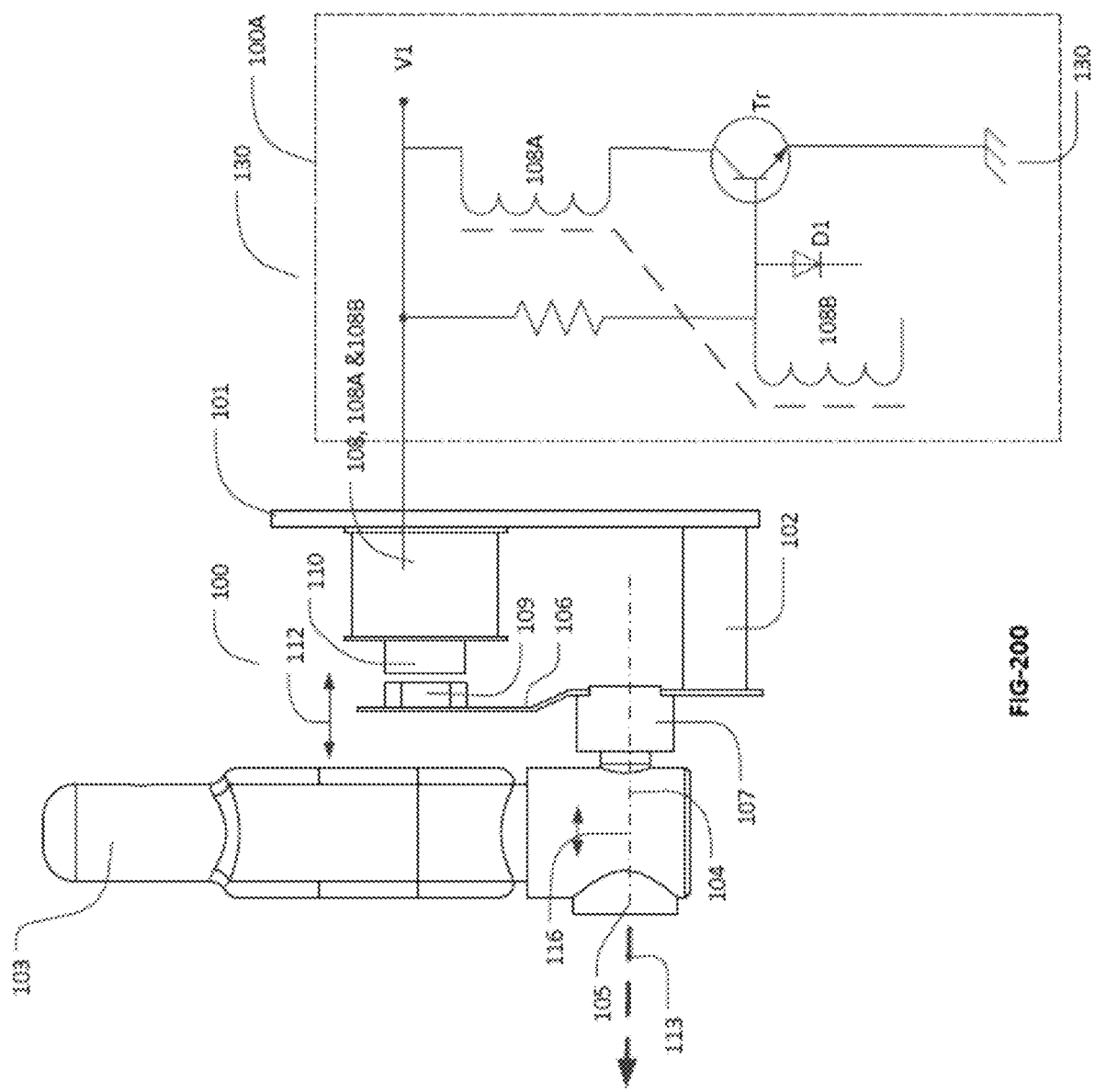
FIG. 200 illustrates a side view of the embodiment of FIG. 100, as well as the electronic circuit thereof.

Methods of administering a liquid formulation of an ophthalmic agent to a topical ocular location of an eye are provided. Aspects of the methods include delivering to the topical ocular location a dose of the liquid formulation that can be wholly accommodated by the tear film of the eye. Devices and kits for practicing the methods are also provided. The methods, compositions and kits find use in a variety of applications, including therapeutic, diagnostic and cosmetic applications.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Methods

As summarized above, aspects of the present disclosure include methods of administering a liquid formulation of an ophthalmic agent to a topical ocular location of an eye of a subject. By topical ocular location is meant a region (i.e., area or domain) of an external surface of an eye, such as a region of a cornea, a region of a conjunctiva, a region that includes both corneal and conjunctival components, etc. In some instances, the topical ocular location is an area or region that is offset relative to the optical axis of the eye. In some instances, the topical ocular location is on either the bulbar or tarsal conjunctiva, or in the conjunctival fornix. In other words, the topical ocular location is one that is displaced from the center of the pupil or the center of the iris. While the magnitude of the distance of the offset/displacement may vary, in some instances the magnitude ranges from 1 to 30 mm, such as 2 to 20 mm, e.g., 5 to 15 mm, including 5 to 10 mm. While the target topical ocular location may vary in size, in some instances the size of the target topical ocular region ranges from 2.5 to 12, such as 3 to 9 mm$^2$.

Aspects of the invention include delivering a dose or volume of the liquid formulation of the ophthalmic agent that can be wholly accommodated by the tear film of the topical ocular location. The tear film of the ocular location is the film that is associated with the topical ocular location. As such, the tear film is the film or layer of tear liquid that is present on the eye surface on which the topical ocular location, e.g., as described above, is located. As the delivered volume of the liquid formulation is a volume that can be wholly accommodated by the tear film of the topical ocular location, it may also be a volume that may be wholly accommodated by the ocular surface that includes the topical ocular location. By "wholly accommodated by the ocular surface" is meant that, upon delivery, the delivered volume is a volume that can be held on the surface of the eye to which it is administered without any excess liquid running off of the surface of the eye and over the eyelid, e.g., in the form of tears. While the volume of a given delivered volume may vary, in some instances the volume ranges from 1 to 15 µl, such as 3 to 10 µl, including 5 to 10 µl. In some instances, the volume of liquid formulation that is administered to the ocular surface does not result in a blinking reflex. As such, delivery of a volume of liquid in accordance with embodiments of the invention does not result in reflex tearing, blepharospasm/blinking, which in embodiments allows for a precise, known amount of active agent to be delivered to the topical location.

An advantage of embodiments of the invention is that because the volume of liquid formulation that is precisely administered to the ocular surface can be wholly accommodated on the ocular surface, exact, known amounts of an ophthalmic agent are delivered to the topical ocular location. As reviewed above, volumes of a liquid formulation are delivered in a manner that minimizes, if not eliminates, reflex tearing and volumetric losses of the liquid formulation. As such, in a given liquid formulation administration, the administered fluid aliquot is exactly what is retained on the ocular surface. Accordingly, methods of the invention allow for delivery of exact known mass amounts of a given ophthalmic agent. In other words, a precise amount of ophthalmic agent is delivered to the ocular surface, in contrast to other administration protocols where a precise, known amount cannot be delivered, predicted or measured because of one or more of loss through reflex blinking or tearing, loss through failure of entire dose to reach ocular surface (e.g., as occurs in delivery of mists or aerosols), etc. In methods of the invention, the amount (mass) of the ophthalmic agent delivered to the ocular surface is a mass equal to the administered volume times the concentration of ophthalmic agent in the administered liquid formulation. For example, if a given administered volume is 10 microliters of a 1% ophthalmic agent (10 mg/mL) solution, then the known mass of ophthalmic agent delivered to the ocular surface is 0.1 mg. Similarly, when delivering 4 microliters of a 2% ophthalmic agent (20 mg/mL) solution in accordance with the invention, the known mass of ophthalmic agent delivered to the ocular surface is 0.08 mg. This ability to know the mass of ophthalmic agent delivered to a topical ocular surface represents a distinct advantage as compared to other methods of delivering active agents to topical ocular locations, e.g., using conventional eye drop protocols or aerosol/mist delivery devices. For example, with a conventional eye drop with a volume of 40 microliters, it is unknown exactly how much of the active agent or drug is actually delivered and maintained on the ocular surface, because (1) the ocular surface cannot hold 40 microliters on its surface, (2) a large portion of the eye drop spills over the lid margin and is wiped with a tissue, and (3) additional drop volume is lost through the lacrimal system, and (4) reflex tearing ensues as a result of the large drop volume and leads to dilution of the drug concentration. With respect to devices that deliver a formulation in mist/aerosol format, not all of the dispensed formulation can be ensured to have landed on the cornea or ocular surface, and not the surrounding periocular surfaces.

While the mass of given ophthalmic agent delivered to a topical ocular location in accordance with embodiments of the invention may vary depending on a number of considerations, including the nature of the agent, the condition to be treated, the age of the subject, etc., in some instances the delivered mass ranges from 0.00001 mg to 10 mg, such as 0.00005 mg to 5 mg, including 0.01 to 1 mg, such as 0.05 to 0.5 mg, including 0.75 to 0.15 mg.

Aspects of the invention include delivering a micro-dose of an ophthalmic agent to a topical ocular location. In some instances, the delivered micro-dose is one that has an efficacy comparable to a reference dosage having a volume that exceeds the capacity of the tear film of the target topical ocular location. The reference dosage in such instances, apart from volume, is otherwise identical to that of the delivered dosage. As such, the concentration of the active agent in the reference dosage is the same as the concentration of the active agent in the delivered dosage. The volume of the reference dosage exceeds that of the delivered dosage. e.g., by 2-fold or greater, such as 3-fold or greater. In some instances, the reference dosage has a volume ranging from 25 to 60 µl, such as 30 to 50 µl. In some instances, the reference dosage is a dosage that is delivered by a standard eye dropper device.

Micro-doses of embodiments of the invention are effective, e.g., to treat an ocular condition for which they are administered, with at least reduced adverse effects, and in some instances without substantial adverse effects, e.g., adverse effects that might otherwise require an additional medicinal agent to counteract the adverse effects and/or result in reduced patient compliance. As such, the magnitude of any adverse effects caused by administration of the micro-doses is reduced and in some instances sufficiently minimal such that no intervention is necessary to ameliorate the adverse effects, e.g., administration of an additional active agent that ameliorates the adverse effects. In some instances, the subject experiences no adverse effects following administration of a micro-dose. As the micro-doses of embodiments of the invention are effective to treat an ocular condition for which they are administered without substantial adverse effects, in some instances the ophthalmic agent is the only active agent present in the micro-dose, such that the micro-dose includes no other active agents, including agents that ameliorate any adverse effects of the ophthalmic agent that treats condition for which it is being administered. For example, where pilocarpine is administered in a micro-dose in accordance with embodiments of the invention, the micro-dose may not include any agents that ameliorate adverse effects of pilocarpine, where such agents include vasoconstrictors, such as oxymetazoline, naphazoline, tetrahydrozoline, and alpha agonists (e.g. brimonidine) and the like.

The ability to deliver precise known amounts in accordance with the invention allows for the delivery of the same dosage or amount of an active agent using a variety of different regimens (the term "regimen" is used its conventional sense to refer to the schedule of doses of an active agent, including the time between doses, the duration of treatment and the amount to be administered each time), where for a given subject a single regimen may be repeatedly used or a number of different regimens may be employed over a given course of treatment. As such, the methods and devices described herein provide for the same dosage of active agent to be delivered by multiple different regimens. For example, with respect to first micro-dose in which a given volume of a drug formulation having a given active agent concentration is administered, the volume of drug formulation and concentration of active agent in the formulation may be varied to obtain a micro-dose that administers the same dosage but by a different regimen. For example, as compared to a first micro-dose, the volume of an active agent formulation that is delivered may be increased and the concentration of active agent in the delivered fluid decreased to the extent that the tolerability and efficacy of the second regimen is superior to that of the first regimen even though the precise dose of active agent administered as determined by weight in micrograms, milligrams or grams of the API is identical amongst the first and second regimens.

As summarized above, methods of the invention deliver a volume of a liquid formulation of an ophthalmic agent, i.e., dose, to an ocular surface. The terms "agent," "compound," and "drug" are used interchangeably herein to refer to a molecule or molecular combination that has a physiological effect upon contact with a subject via administration to a topical ocular location of the subject. The active agent may include one or more functional groups that provide for structural interaction with the intended target. Functional groups of interest include, but are not limited to: groups that participate in hydrogen bonding, hydrophobic-hydrophobic interactions, electrostatic interactions. Specific groups of interest include, but are not limited to amines, amides, sulfhydryls, carbonyls, hydroxyls, carboxyls, etc. Active agents of interest may include cyclical carbon or heterocyclic structures and/or aromatic or polyaromatic structures substituted with one or more of the above functional groups. Also of interest as moieties of active agents are structures found among biomolecules, including peptides/proteins, saccharides, fatty acids, steroids, purines, pyrimidines, nucleic acids, derivatives, structural analogs or combinations thereof. Active agents of interest include small, medium and large molecule active agents. Small molecule active agents are those active agents having a molecular weight ranging from 18 to 2500 daltons, such as 1000 to 1500 daltons and including 250 to 1000 daltons. Medium molecule active agents are those active agents having a molecular weight ranging from 2500 to 10,000 daltons, such as 4,000 to 8,000 daltons and including 5000 to 7000 daltons. Large molecule active agents are those active agents having a molecular weight of 10,000 daltons or more, such as 100,000 daltons or more, where in certain instances these large molecule active agents range from 1 million to 30 million daltons, such as 5 million to 20 million daltons and including 10 million to 15 million daltons. Examples of active agents that may present in the liquid formulation include, but are not limited to: anti-microbial agents (including but not limited to antibiotics (e.g., Sulfacetamide, Trimethoprim, Ofloxacin, Gentamicin, Neomycin, Tobramycin, Polymyxin, Ciprofloxacin, Gatifloxacin, Levofloxacin, Moxifloxacin), antivirals, anti-fungals (e.g., Polyenes, such as Amphotericin B (AMB)-polyene macrolide antibiotic and Natamycin, and Azoles, such as Miconazol, Ketoconazole, Itraconazole, Flucanazole, Voriconazole, Posaconazole and Echinocandins), anti-inflammatories (including but not limited to steroids (e.g., Corticosteroids, such as Prednisolone, Prednisolon. Dexamethasone, Loteprednol, Difluprednate, Fluorometholone, Rimexolone and Medrysone) and non-steroidal anti-inflammatory drugs (NSAIDS, such as Ketorolac), etc.), anti-allergy agents (including but not limited to anti-histamines (e.g., Azelastine hydrochloride, Emedastine difumarate and Levocabastine) and mast cell stabilizers, etc.), vasoconstrictors, anesthetics (e.g., Lidocaine, Tetracaine Proparacaine), analgesics, intraocular pressure lowering agents (including but not limited to prostaglandin analogs (e.g., Bimatoprost, latanoprost, Travoprost and Tafluprost), ROK inhibitors (e.g., Netarsudil), beta blockers (e.g., Levobunolol, Timolol, Betaxolol, Carteolol and Metipranolol), carbonic anhydrase inhibitors (e.g., Brinzolamide, Methazolamide and Dorzolamide) and alpha agonists (e.g., Apraclonidine hydrochloride and Brimonidine tartrate), etc.), lubricants (including but not limited to saline, polymer solutions, proteoglycans, glycosaminoglycans, carbohydrates, etc., such as found in artificial tears), mydriatic (pupil dilating) agents, iodine derivatives, cholinergic agents (e.g., as described in greater detail below), including parasympltholytic agents, parasympathomimetic agents and sympathomimetic agents (e.g., tetrahydrozoline), anti-cholinergic agents, including both long acting and short acting agents (e.g., atropine, tropicamide, etc.), and/or various combinations thereof.

In some instances, the ophthalmic agent is a cholinergic agent. The term "cholinergic agent" refers to any active agent that inhibits, enhances, or mimics the action of the acetylcholine, where cholinergic agents may include both nicotinic and muscarinic classes. Cholinergic agents include agents that modulate the parasympathetic nervous system, i.e., that part of the autonomic nervous system that contracts smooth muscles, dilates blood vessels, increases bodily secretions, and slows the heart rate. In some instances, the cholinergic agent is a miotic agent. Miotic agents are agents that cause contraction of the pupil of the eye. Miotic agents of interest include, but are not limited to, pilocarpine, carbochol, physostigmine, echothiophate, methacholine, moxisylyte and pharmaceutically acceptable salts thereof, and combinations thereof. In some instances, the cholinergic agent is a muscarinic agonist. Muscarinic agonists are agents that activate the activity of a muscarinic acetylcholine receptor, and in some instances the $M_3$ muscarinic receptor subtype. Muscarinic agonists of interest include, but are not limited to: pilocarpine, carbochol, physostigmine, methacholine, acelidine, arecoline, and cevimeline, and pharmaceutically acceptable salts thereof, and combinations thereof. As indicated above, in some instances the cholinergic agent is both a miotic agent and a muscarinic agonist. Where the ophthalmic agent that is delivered to the ocular surface is a cholinergic agent, methods and devices as described herein may be employed to treat any condition for which a cholinergic agent has efficacy.

Additional drugs and agents which may be utilized with the devices described may include any number of the agents disclosed in further detail in U.S. Pub. 2017/0344714 and U.S. Pat. No. 9,087,145 the disclosures of which are herein incorporated by reference.

As reviewed above, the liquid formulation includes the ophthalmic agent in a liquid delivery vehicle. The liquid delivery vehicle may be an aqueous delivery vehicle, e.g., a pharmaceutically acceptable aqueous vehicle. In addition to water the aqueous delivery vehicle may include a number of different components, including but not limited to: salts, buffers, preservatives, solubility enhancers, viscosity modulators, colorants, etc. Suitable aqueous vehicles include sterile distilled or purified water, isotonic solutions such as isotonic sodium chloride or boric acid solutions, phosphate buffered saline (PBS), propylene glycol and butylene glycol. Other suitable vehicular constituents include phenylmercuric nitrate, sodium sulfate, sodium sulfite, sodium phosphate and monosodium phosphate. Additional examples of other suitable vehicle ingredients include alcohols, fats and oils, polymers, surfactants, fatty acids, silicone oils, humectants, moisturizers, viscosity modifiers, emulsifiers and stabilizers. The compositions may also contain auxiliary substances, i.e. antimicrobial agents such as chlorobutanol, parabens or organic mercurial compounds; pH adjusting agents such as sodium hydroxide, hydrochloric acid or sulfuric acid; and viscosity increasing agents such as methylcellulose. An exemplary final composition is sterile, essentially free of foreign particles, and has a pH that allows for patient comfort and acceptability balanced with a pH that is desirable for optimum drug stability. An exemplary "pharmaceutically acceptable vehicle" is an "ophthalmically acceptable vehicle" as used herein refers to any substance or combination of substances which are non-reactive with the compounds and suitable for administration to patient. In an exemplary embodiment, the vehicle is an aqueous vehicle suitable for topical application to the patient's eyes. In various embodiments, the vehicle further includes other ingredients which may be desirable to use in the ophthalmic compositions of the present invention include antimicrobials, preservatives, co-solvents, surfactants and viscosity building agents. The concentration of the cholinergic agent in a given liquid formulation of a micro-dose may vary.

In some instances, the liquid formulation is preservative free. By "preservative-free" is meant that the formulations do not include any preservative agents, such as but not limited to, antimicrobial agents such as benzalkonium chloride (BAK), chlorobutanol, sodium perborate, and stabilized oxychloro complex (SOC), parabens and organic mercurial compounds.

An exemplary final composition is sterile, preservative-free, essentially free of foreign particles, and has a pH that allows for patient comfort and acceptability balanced with a pH that is desirable for optimum drug stability. An exemplary "pharmaceutically acceptable vehicle" is an "ophthalmically acceptable vehicle" as used herein refers to any substance or combination of substances which are non-reactive with the compounds and suitable for administration to patient. In an exemplary embodiment, the vehicle is an aqueous vehicle suitable for topical application to the patient's eyes. In various embodiments, the vehicle further includes other ingredients which may be desirable to use in the ophthalmic compositions of the present invention include antimicrobials, preservatives, co-solvents, surfactants and viscosity building agents.

In some embodiments, the concentration of ophthalmic agent in the liquid formulation of the micro-dose ranges from 50 ng/ml to 100 mg/ml. For example, where the cholinergic agent is pilocarpine, the concentration of pilocarpine in the liquid formulation may range from 5 to 50 mg/ml, such as 10 mg/ml (1%), 20 mg/ml (2%) and 40 mg/ml (4%).

The liquid formulation, e.g., in the form of a micro-dose, may be administered to the topical ocular location using any convenient protocol. In some instances, the delivered volume is administered to the topical ocular location as a stream, where the stream may be a continuous stream of liquid (i.e., a stream that is not made up of individual droplets) or a discontinuous stream of liquid, e.g., a collimated stream of individual droplets, a series of streams, etc. As the stream, whether continuous or discontinuous, may be collimated, in certain embodiments the liquid formulation contacts a limited portion of the external surface of the eye before spreading across more of the eye surface, where is some instances the limited contact portion is 50% or less, such as 40% or less, including 30% or less, e.g., 25% or less, 20% or less, 15% or less, including 10% or less, e.g., 5% or less of the external surface of the eye. Embodiments of the invention provide for accurate delivery of the stream to a defined location, such that the stream is precisely administered to a desired location of the ocular surface. As the stream may be delivered as a collimated stream, in such instances substantially all, if not all, of the liquid formulation released from the device is delivered to the ocular surface, in contrast to other delivery modalities such as mists and aerosols where not all of the fluid emitted from the device reaches the ocular surface, but instead at least some of which is applied to the surrounding periocular surfaces. Where the stream is a continuous stream of liquid, the stream diameter may vary, and in some instances ranges from 0.05 to 0.50 mm, such as 0.070 to 0.130 mm. In some instances, the stream diameter is substantially constant along its length from its origination point to the topical ocular location, such that any magnitude of difference in diameter is, in some instances, 1 mm or less, such as 0.5 mm or less, e.g., 0.25 mm or less. In such instances, the stream may be collimated, such that it spreads minimally, if at all, as it propagates from the orifice of the device to the ocular surface. Where the stream is a discontinuous stream of individual droplets, the volume of the individual droplets may vary, ranging in some instances from 50 to 1500 µl, such as 100 to 1000 µl. Where droplets are administered, the diameter of a given droplet may vary, ranging in some instances from 20 to 1000 µm, such as 50 to 750 µm, including 100 to 500 µm. The duration of stream delivery during a given administration event may vary and is selected so as to provide the desired delivered micro-dose, e.g., as described above. In some instances, the duration of stream delivery, i.e., the duration of administration, ranges from 20 to 2000 msec, such as 50 to 1000 msec, including 75 to 500 msec, such as 50 to 200 msec, including 100 to 150 msec. The volume that is delivered may be varied as a function of pulse duration, where the pulse duration may be fixed or variable. The velocity of the administered stream may vary and is generally above the minimum exit velocity of the fluid from the aperture of the device used to administer the stream, e.g., as described in greater detail below. The "minimum exit velocity" is as defined in Linblad and Scheider, "Production of uniform-size liquid droplets," J. Scientific Instruments (1965) 42:635. (see equation 2 described therein). In some instances, the exit velocity is 20% or more above the minimum exit velocity and in some instances is 300% or less above the minimum exit velocity. For example, for an aperture size of 125 micron the minimum exit velocity is 194 cm/sec but the selected velocity may be at least 30% higher, i.e. at least 252 cm/sec. In some instances, the velocity ranges from 10 to 500 cm/sec, such as 20 to 250 cm/sec and including 50 to 150 cm/sec.

The delivered volume of liquid formulation, e.g., micro-dose, may be administered to the topical ocular location using any convenient protocol. In some instances, the delivered volume is administered to the topical ocular location by an individual other than the subject, e.g., where the delivered volume is administered by a health care professional, such as a physician or nurse or other health care provider. In other instances, the delivered volume is self-administered by the subject, e.g., where the subject administers the volume to a topical ocular location of one of the subject's own eyes.

While the nature of the device employed to administer a give volume of a liquid formulation may vary, in some instances the device is a handheld device. By handheld device is meant that the device is dimensioned and has a weight such that it may be comfortably held by an average adult human hand. In some instances of handheld devices, the device has a longest dimension ranging from 10 to 500 mm, such as 20 to 250 mm, including 50 to 100 mm, such as 70 to 85 mm, and a weight ranging from 10 to 2000 g, including 20 to 1000 g, such as 25 to 500 g, e.g., 40 to 100 g.

In some instances the device is one that includes: (1) a container comprising an amount of the liquid formulation of the cholinergic agent and one or more apertures; and (2) an actuator configured to emit a volume, e.g., micro-dose, of the liquid formulation from the container through the one or more apertures. The container may have any convenient configuration, and may be made of any convenient material, e.g., glass or plastic. The container may be configured to hold a single delivered dose or multiple delivered doses, e.g., where the container comprises a volume of the liquid formulation sufficient to provide multiple delivered doses. As such, the volume of liquid formulation that the container is configured to hold may vary ranging in some instances from 100 µl to 10 ml, such as 100 to 2000 µl, including 120 to 800 µl.

The actuator component is a component that imparts energy to the liquid formulation sufficient to produce the desired stream (e.g., as described above) by forcing the liquid formulation through the one or more apertures. In some instances, the actuator is a component that is configured to vibration energy to the contents of the container, where the oscillation frequency of the vibrational energy may vary. In some instances, the oscillation frequency is an ultrasonic frequency, ranging in some instances from 20 to 800 KHz, such as 20 to 35 KHz. In some instances, the frequency is in the audible range, such as from 20 to 20000 Hz, e.g., 50 to 10000 Hz, including 500 to 1000 Hz.

While the nature of the actuator component may vary, in some instances devices that include an electromagnetic actuator are employed. In embodiments of such devices, an electromagnetic actuator imparts an oscillation amplitude at low frequency, which in some instances is within the audible range (e.g., 20 to 20,000 Hz). In some instances, the electromagnetic actuator operates in the audio range of frequencies, but produces low audible tone, generally 30 dB or lower. At the same time, the device emits fluid from a sufficiently large nozzle at sufficiently low velocity to minimize the discomfort associated with topical delivery to the eye. Further details regarding such electromagnetic devices are provided in provisional application Ser. Nos. 62/693,818 filed Jul. 3, 2018 and 62/814,773 filed Mar. 6, 2019; the disclosures of which are herein incorporated by reference.

An embodiment of an electromagnetic actuated device is illustrated in FIGS. 100 to 300. Referring to FIG. 100, which illustrates the electromagnetic dispensing device (100) of the present invention, device (100) includes an ampoule (103) containing a fluid to be dispensed and further includes an electromagnetic transducer (113) that is configured to oscillate the ampoule such that the fluid is dispensed through aperture (116 at the lower part of the ampoule.

Transducer (113) comprising a base plate (101), electromagnet (115) and a permanent magnet (109). Electromagnet (115) comprising a ferromagnetic core pin (110) and a coil (108) that is wound around the core pin. Permanent magnet (109) is positioned in a close proximity to the electromagnet core pin (110) and is suspended by a flexible cantilever beam (106). An alternating magnetic field generated by coil (108) produces magnetic force and mechanical oscillations of permanent magnet (109) and the flexible cantilever beam (106) that supports it. Cantilever beam includes an anchor (107) which support and transmits the oscillation of the cantilever beam to the ampoule. The device further includes a standoff support pin (102) that extends from the base plate (101) and provides a support to the cantilever beam (106).

In the illustrated embodiment, permanent magnet (109) is positioned at the free end of cantilever beam at a distance of (d2) from the cantilever beam support (102) while the ampoule support anchor (107) is at a distance of (d1) from the beam support (102). In this way a mechanical advantage is obtained, and the force applied to the ampule is amplified by the ratio of the distances d2/d1 relative to the force applied to the permanent magnet. In the illustrated embodiment the ampoule contains 1 mL of aqueous solution and has a mass of approx. 1 gm. Accordingly the force that is required to oscillate the ampoule at an amplitude of approximately 20-60 mm is about 0.2N to 1N. In the illustrated embodiment, the distance d2 is 13.5 mm and distance d1 is 1.35 mm. The ratio d2/d1 is about 10, and the oscillation amplitude is between 20 µm to 60 µm, depending on the input voltage. In the illustrated embodiment, the diameter of the dispensing aperture ranges between 200 µm and 350 µm, and such large aperture dispenses only at high oscillation amplitude.

In the illustrated embodiment the ferromagnetic core (110), base plate (101) and support pin (102) are made of a soft magnetic material, such as 4750 alloy, or other alloys that have low corrective force and minimal magnetic hysteresis can be used.

Ampoule (103) is oriented such that the dispensing nozzle (116) is aligned with the oscillation amplitude of the cantilever beam (106). The oscillations generate pressure fluctuation inside the ampoule and fluid is ejected from nozzle (116) as illustrated by the arrow (105)

Permanent magnet (109) may be made of a rare-earth magnetic material, such as Neodymium N35, N38, N42, Samarium Cobalt or the like. Non-rare-earth alloy such as iron, nickel and cobalt may also be used.

Referring now to FIG. 200, this figure shows magnetic transducer (100) and further includes a diagram of the electrical circuit that generates alternating electrical signal from a DC source, such as a battery cell.

Electromagnetic transducer (100) includes a circuit (100A) which produces alternating current which is fed to the coil (108) to generate a magnetic force which oscillates permanent magnet (109). Coil (108) defines two separates magnetic coils, the first is primary coil (108A) and the second is detection coil (108B). Both coils (108A) and (108B) are wound around the iron core (110). When DC voltage is connected to the primary coil (108A) current flows and the electromagnetic force that is developed pulls permanent magnet (109) toward core (110). At the same time the current in the primary coil (108A) produces transient, time-dependent electromagnetic induction, which induces electromotive force (EMF) and electrical current in the detection coil (108B), the current is fed to a bipolar transistor (Tr) which switches off the current from the primary coil (108A) by pulling it to the ground (130). As a result, magnetic force returns to zero and magnet (109) return to its normal position. Subsequently, primary coil (108A) turns on again and pulls back the magnet. In this way the alternating magnetic field is generated using a DC input voltage from a DC battery. Transistor (Tr) is an NPN general purpose amplifier, such as Fairchild model 2N3904. The circuit further includes a Zener diode (D1) that regulates the voltage. Magnetic coil (108A) and (108B) have an inductance that ranges from 1-10 mH and are configured to generate a magnetic field to oscillate the magnet (109). Generally, the mass of magnet (109) is small to reduce the inertial load and increase the oscillation amplitude. In one embodiment, the mass of permanent magnet (109) is 0.075 gm. Beam (106) is made of stainless steel alloy 304 having a thickness of 0.2 mm, a width of 5 mm and a free length of 13.5 mm. In the illustrated embodiment, the beam has a natural frequency of about 523 Hz while the driving frequency of magnetic oscillator is about 1100 Hz.

Figure 300A:
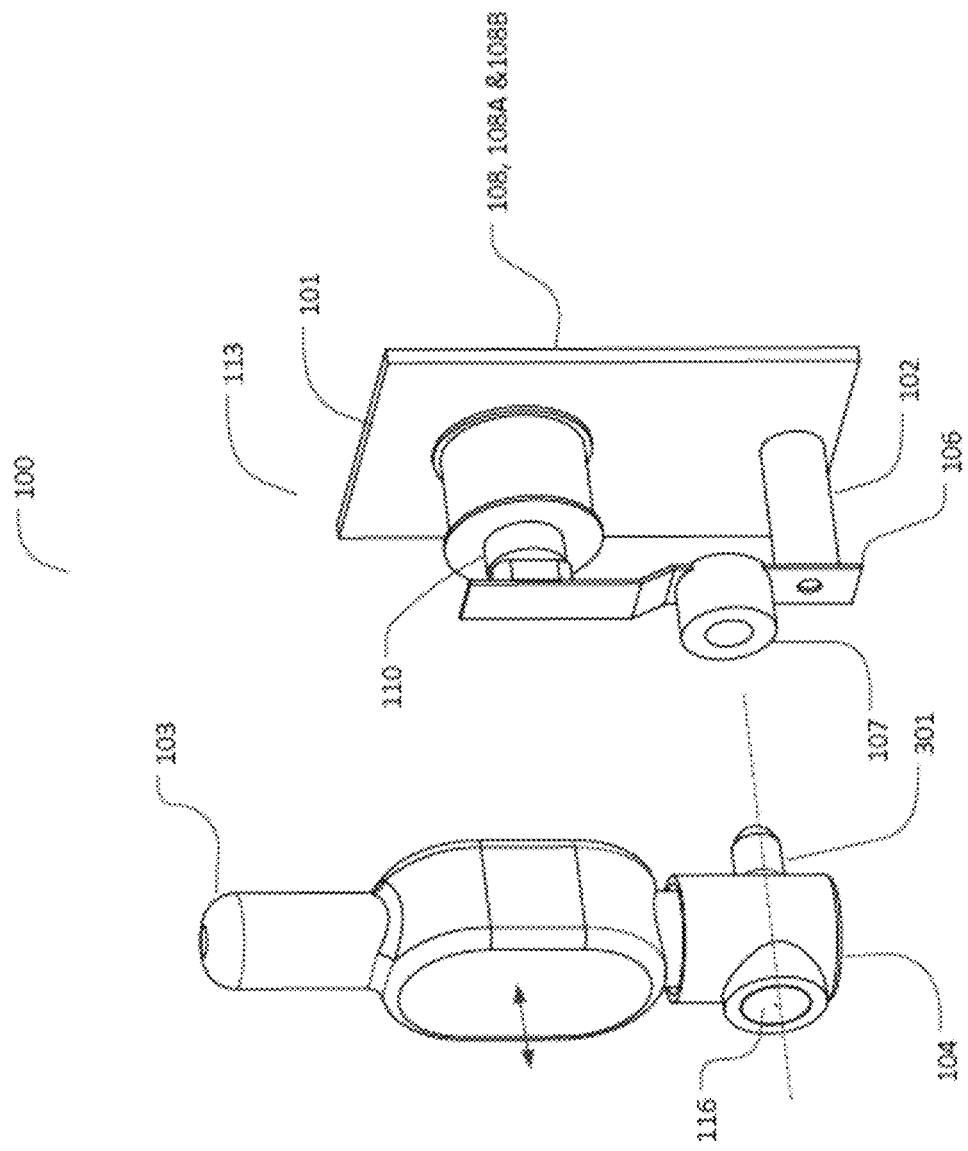
FIG. 300A illustrates an exploded view of the embodiment of FIG. 100 and FIG. 200 showing the ampule and the magnetic transducer separately.

FIG. 300A illustrates an exploded prospective view of the dispensing device (100), showing the ampoule (103) and the electromagnetic transducer (113) separately. It can be seen that ampule (103) includes a pin member (301) that is inserted into anchor member (107) in a tight interference fit. In this way the oscillations that are generated by the transducer are transmitted to the ampoule.

Where desired, e.g., to provide for a preservative free liquid formulation (such as described above, the device may include a closure for selectively sealing the aperture when fluid is not being ejected therethrough. In such instances, the actuator may be configured to operate the closure so as to at least reduce, if not prevent, ingress of outside materials or contaminants into the reservoir, such that the ophthalmic formulation present in the reservoir does not require a preservative (e.g., where a preservative-free ophthalmic formulation is present in the reservoir). In some instances, the closure includes a sealing structure configured to mate with the aperture in a sealing relationship, where the sealing structure is movable relative to the aperture between a first position that seals the aperture and a second position that does not seal the aperture. The sealing structure may have any convenient configuration. In some instances, the sealing structure has a conical structure. In such instances, the conical sealing structure may have a height ranging from 0.5 to 5.0 mm, such as 0.75 to 1.5 mm and a bottom diameter ranging from 0.4 to 4.0 mm, such as 1.5 to 2.5 mm. In other embodiments, the sealing structure may be a rounded sealing structure, which in some instances may have a halfspherical structure, with a bottom diameter ranging from 0.4 to 4.0 mm, such as 1.5 to 2.5 mm. Where desired, the sealing structure, e.g., conical sealing structure, rounded sealing structure, etc., may be present at the end of an elongated member, which functions to translate motion from the actuator to the sealing structure and thereby provide movement of the sealing structure relevant to the aperture. The elongated member may have any convenient configuration, and may be configured to interact with one or more additional components to provide or the desired motion translation from the actuator to the sealing structure. In some instances, the elongated member has a rod configuration. In such instances, the rod portion may have any convenient dimensions, ranging in length in some instances from 0.5 to 8.0 mm, including 1.0 to 2.5 mm and ranging in diameter in some instances from 0.5 mm to 5.0 mm, including 0.7 to 2.0 mm. When the closure includes a conical sealing structure positioned at the end of a rod, the closure may be referred to as a pin. The sealing structure, as well as elongated member when present, may be fabricated from any convenient material, including metallic or polymeric materials. As illustrated, the fluid package may have an expanded region comprising the reservoir and a neck region comprising the aperture. In such instances, the sealing structure is present in the neck region. The configuration of the sealing structure in the neck region may vary, e.g., depending on how the actuator is configured to move the sealing structure relative to the orifice. In some instances, the sealing structure is present at the end of an elongated member, e.g., as described above. In such instances, a second end of the elongate structure may be stably associated with attachment location of an inner surface of the neck region, e.g., where the attachment region is movable relative to the orifice so as to provide movement of the elongated member and sealing structure relative to the aperture. An example of such an attachment location is one that is made up of a flexible material, such as a membrane or diaphragm. In such instances, force can be applied from outside the package to provide for the desired movement of sealing structure relative to the aperture, e.g., between first and second locations. In other embodiments, the elongated member may be operably associated with a lever that extends through an orifice in the neck region. In such instances, the lever may be moved, e.g., by the actuator, from a location external to the fluid package and thereby move the sealing structure in the neck region relative to the aperture, as desired. In these embodiments, the dimensions of the lever orifice may vary as desired to accommodate the dimensions of the lever, ranging in some instances from 0.5 to 2.5 mm, such as 1.0 to 1.5 mm. To prevent fluid from leaking from the fluid package, the lever may be sealed in the orifice, e.g., with an O-ring. In such embodiments, the lever may be configured not to move into and out of the orifice, but instead pivot relative to the orifice wall. Where desired, a bias element may be provided which biases the sealing structure into the aperture when fluid is not be ejected through the aperture, such that the sealing structure seals the aperture. For example, a spring may be provided which biases the sealing structure into the aperture unless the actuator is active, such that sufficient force is applied against the bias to move the sealing structure out of the aperture. Further details regarding embodiment of such sealing structures and their use with delivery devices of the invention may be found in U.S. Provisional Patent Application Ser. No. 62/814,773 filed Mar. 6, 2019; the disclosure of which is herein incorporated by reference.

Figure 300C:
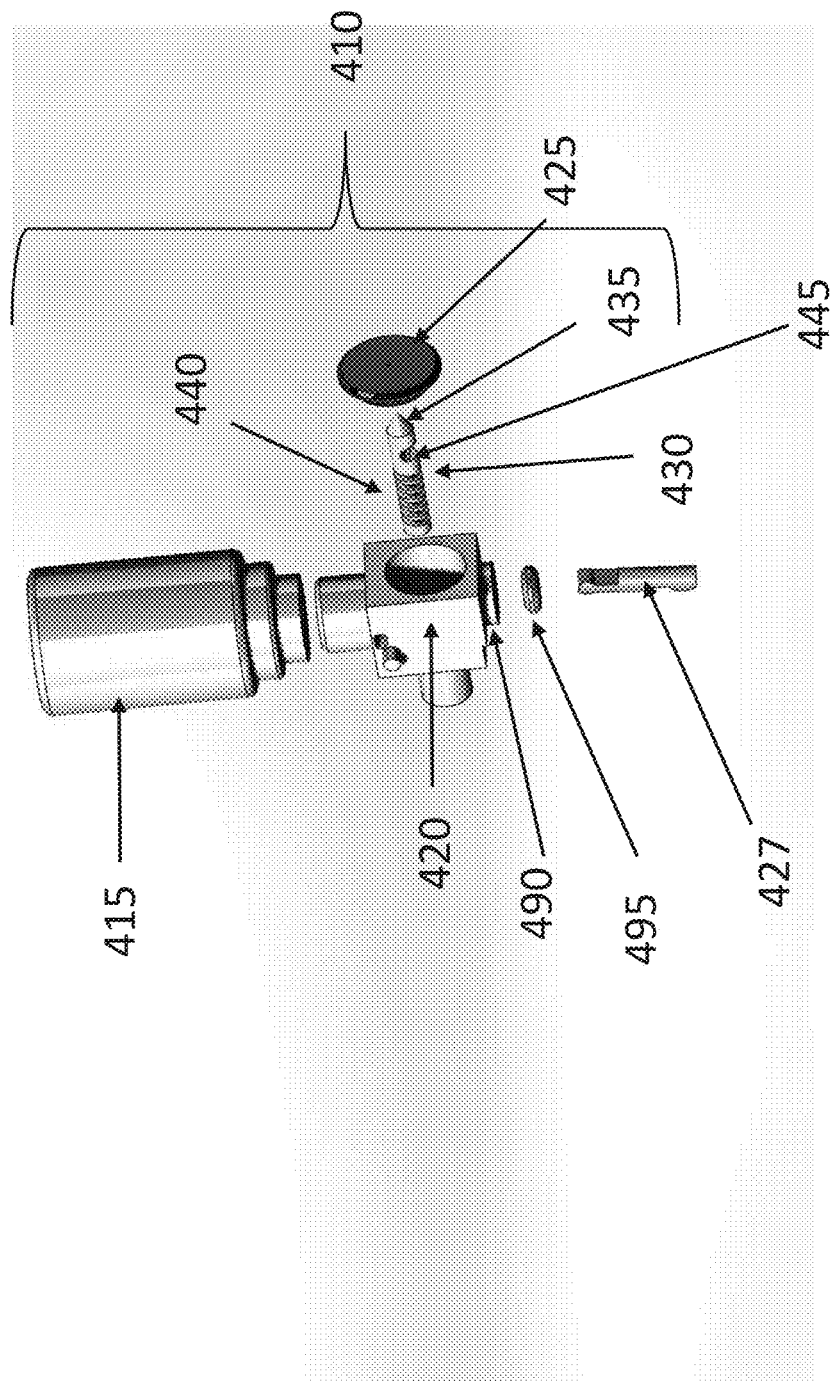
Figure 300D:
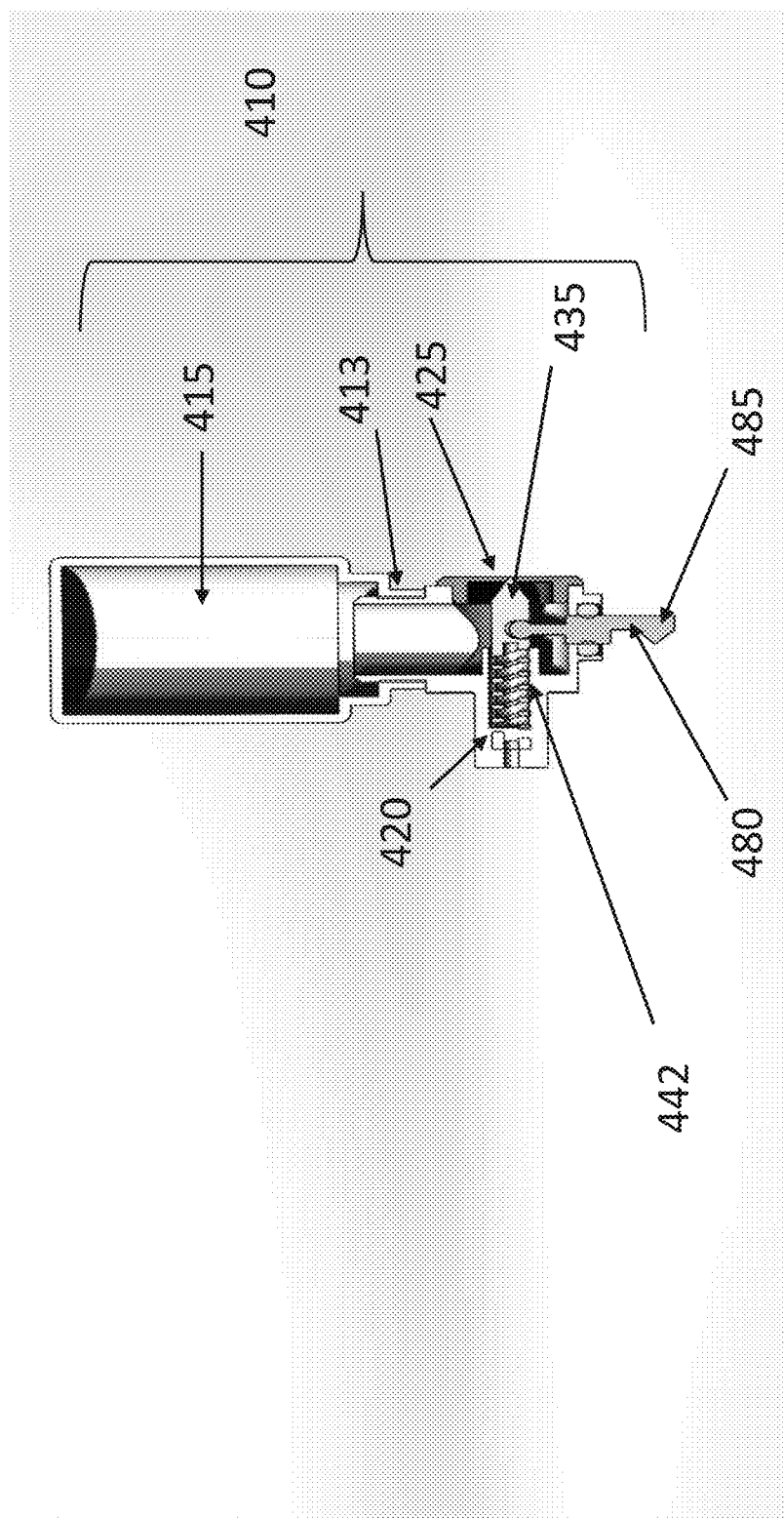

FIGS. 300B to 300D provide more detailed views of a fluid package and operation of the closure to seal the orifice when fluid is not being ejected from the orifice. In FIG. 300B fluid package (410) is shown operably coupled to actuator (450). Fluid package (410) includes an expanded region (415) that includes the reservoir, which is a standard ophthalmic bottle, and neck region (420) press fit onto the opening of the ophthalmic bottle. The neck region includes aperture plate (425) that includes a single aperture. Also shown is lever (427) that connects to a closure in the form of pin present inside the neck region. Actuator (450) includes solenoid housing part (460) and drive coil (470) that moves lever (427), where lever movement in turn moves the pin from a first position that seals the aperture to a second position where the aperture unsealed and fluid can be ejected therethrough.

FIG. 300C provides an exploded view of fluid package (410), which includes ophthalmic bottle (415) and neck region (420). Neck region includes aperture plate (425) and closure member (430), where the closure member is in the form of a threaded pin having a conical sealing structure (435) at one end and threads (440). Also shown is groove (445) that is configured to operably mate with lever (427). Lever (427) extends into neck region (420) via orifice (490) and is sealed by O-ring (495).

FIG. 300D provides a cutaway view of fluid package (410) illustrating the internal assembly thereof. As shown, neck region (420) is fit into the opening (413) of ophthalmic bottle (415). Spring (442) urges conical sealing structure (435) of pin closure member (430) against the aperture of aperture plate (425) to seal the aperture. When fluid is to be ejected through the aperture, external end (485) of lever (427) is moved towards the aperture plate which moves the pin and conical structure thereof away from the aperture plate, thereby unsealing the aperture and allowing for fluid to be ejected therethrough. As described generally above, the conical sealing structure and/or aperture may include an antimicrobial material.

In yet other embodiments, devices in which the actuator component is a piezoelectric actuator are employed. Examples of piezoelectric actuator devices that may be employed in embodiments of the invention are further described in: U.S. patent application Ser. No. 14/992,975 filed Jan. 11, 2016 and published as U.S. Pat. Pub. 2016/0199225; U.S. patent application Ser. No. 15/094,849 filed Apr. 8, 2016 and published as U.S. Pub. 2016/0296367; U.S. patent application Ser. No. 15/874,377 filed Jan. 18, 2018 and published as U.S. Pub. 2018/0207030; International Application Serial No. PCT/US2018/064529 filed Dec. 7, 2018; U.S. Prov. Pat. App. 62/656,552 filed Apr. 12, 2018; and U.S. Prov. Pat. App. 62/693,818 filed Jul. 3, 2018; which applications are incorporated herein by reference.

FIG. 400A and FIG. 400B illustrate a prospective view and an exploded prospective view of piezoelectric actuator fluid dispensing device. Device (400) comprises a piezoelectric clamping actuator (10) and separable disposable fluid-filled ampule (20). Ampule (20) comprises a thin-walled thermoplastic package which includes a bulb section (21) and a neck section (22). Neck section (22) has a cylindrical shape with a circular cross-sectional shape. Other cross-sectional shapes, such as an oval shape, are also possible. One or more apertures (23) are positioned on the wall of the neck section. Piezoelectric clamping actuator (10) is configured to clamp the circumference of the neck section (22) adjacent to the aperture (23) while at the same time apply cycles of oscillations in the clamping direction against the wall of the ampule as illustrated by the arrows (14A) and (15A). Oscillation of ampoule neck (20) cyclically deforms the circular shape of the neck section into elliptical shape and produce cycles of acoustic pressure in the fluid within the neck (22) and ejection of droplets (24) from an aperture (23). In one embodiment, the neck of the ampule (22) is inserted into the piezoelectric clamping actuator (10) by light force, such as less than 10 newtons. Once inserted, the cylindrical neck (22) engages in an interference fit with the clamp (10) which facilitates transmission of the oscillation amplitude to the ampule neck. In some instances, the oscillation amplitude is less than 2 microns.

The above described electromagnetic and piezoelectric mechanisms may be provided in any convenient device configuration. In some instances, the device configuration, in addition to the components described above, includes an alignment system, e.g., which provides for the stream of liquid formulation to be accurate delivered to a specific location on the topical surface. In some instances, the alignment system is an image-based alignment system configured to align fluid ejected through an aperture of the fluid package with a target location, such as a target ocular location (e.g., as described in greater detail below). The alignment systems are systems that allow user, such as the subject to which the fluid is to be administered, to align the aperture with the target location such that the ejected fluid is accurately delivered to the target location upon actuation of the device. The alignment system is, in some instances, configured so that a user may self-administer the fluid from the device following alignment by the user of the device. As summarized above, the alignment systems may be image-based alignment systems. By "image-based" alignment system is meant that alignment of a delivery device with a target location includes visualization of an image, e.g., a picture or a reflection, by a user, e.g., the subject to which fluid is delivered during a self-administration protocol.

In some instances, the image-based alignment system is a reflective surface (i.e., mirror) image-based alignment system, where such systems include one or more reflective surfaces or mirrors, and in some instances include a single reflective surface or mirror. In some instances, the reflective surface has a curved shape which defines a focal point, i.e. comprising a concave mirror.

Typically, the most visible parts of the eye, when looking in a mirror, are the iris, conjunctiva, sclera (through the conjunctiva), and cornea. Ocular tissue in the focal plane of the concave spherical mirror will appear in focus when the mirror is placed at the focal distance (F) from that tissue The focal point (P) is the intersection of the focal plane with the optical axis of the mirror. One method for delivering fluid to a targeted region may generally comprise positioning a reflective surface having a curved shape into proximity with the targeted region located upon a surface of an eye until a reflection of the eye in the reflective surface appears focused to a subject, wherein a focal plane defined by the reflective surface is coincident with the eye when the reflection appears focused. Once positioned, the method may include actuating a fluid delivery assembly to emit a fluid from one or more apertures so that fluid is delivered to the target location on the eye.

In some instances, the reflective surface defines one or more openings therethrough. In such systems, the system may also include a fluid delivery assembly configured to emit a fluid from one or more apertures which are aligned with the one or more openings, wherein the system is configured to emit the fluid through the one or more openings and towards or in proximity to the focal point. In some instances, the fluid delivery assembly is configured to emit a fluid from one or more apertures which are aligned with one or more openings defined through the reflective surface such that the fluid is directed towards or in proximity to the focal plane and upon the targeted region. In another variation, a system for aligning a fluid delivery assembly relative to a targeted region on an eye of a subject may generally comprise a concave mirror having a reflective surface, wherein the mirror defines a focal plane and one or more openings through the mirror for fluid delivery, and a fluid delivery assembly configured to emit a fluid from one or more apertures which are aligned with the one or more openings such that the fluid is ejected through the one or more openings and towards or in proximity to the focal plane.

Instead of a concave mirror, the reflective imaging assembly may include a flat mirror coupled with a suitable lens that provides for alignment by a user, e.g., as described above and in greater detail below.

Whether the reflective surface is curved or flat, the alignment system may be configured such that in self-administration protocols where the target location is an ocular surface, the user may focus an image of the eye that includes the target location when aligning the fluid delivery device. As such, the same eye that includes the target ocular location is employed by the user to align the fluid delivery device, e.g., by focusing and centering the eye in the mirror of the alignment system.

The dimensions of the reflective surface of such image-based alignment systems may vary, as desired. In some instances, reflective surface has a longest dimension, e.g., diameter, that ranges from 10 to 30 mm. In some instances, the dimensions are such that a subject does not view the entire eye that includes the target ocular location in the mirror. In such instances, the longest dimension, e.g., diameter, may range from 10 to 15 mm, such as 10 mm, 11 mm, 12 mm, 13 mm, 14 mm or 15 mm.

In some embodiments, the fluid delivery devices include a housing with which the various components of the device, e.g., as described above, are associated. The housing may have any convenient configuration, and in some instances has a longest dimension ranging from 50 to 100 mm, such as 70 to 85 mm. The housing may have any convenient shape, where shapes of interest include those that allow for ready handling and use of the device. In some instances, the housing has an approximately rectangular cuboid shape. The housing may be fabricated from any convenient material, such as a plastic or metal material.

While the various components of the device may be associated with the housing component in any convenient manner, in some instances the fluid package and actuator components are present inside the housing, and least a portion of the image-based alignment system is associated with a surface of the housing, e.g., so that the image-based alignment system may be viewed by a user during use.

In some instances, the housing includes a movable cover, e.g., which covers the apertures and/or alignment system when the device is not in use. The cover may be configured to move between closed and open positions, where upon moving the cover from the closed to the open position, the device is transitioned to a configuration where it may be employed to deliver fluid. In some instances, movement of the cover from the closed to the open position may result in the device transitioning from an inactive to active state. For example, movement of the cover from the closed to the open position may results in activation of the actuator component.

In some instances, the device includes one or more illumination sources. Any convenient illumination source may be employed, where such sources include, but are not limited to, light emitting diodes (LEDs), and the like. When present, the illumination source may take a variety of different configurations. For example, it may be distinct from any other component of the device, such as the alignment system. Alternatively, it may be associated with another component of the device. For example, it may be associated with the alignment system of the device, such as at least partially bounding, if not completely bounding the alignment system of the device. When present, the illumination source may serve a variety of different functions, such as illuminating the target location in a reflective surface of the alignment system, indicating that the device is aligned with the target location, indicating that the device is within a predetermined distance of the target location, indicated that the device is ready to deliver fluid, indicating the amount of fluid in the fluid package (e.g., full, partially full, empty), and the like.

In some embodiments, illumination is presented as a circular LED, or single or multitude of LED lights in optional pattern (e.g. circular pattern around a circular mirror). The LED light(s) are configured to produce a light reflection on the corneal surface, and will be superimposed on the reflection of the patient's eye. The light reflection, as well as the central aperture element, will appear to be overlayed over the iris and pupil of the patient's eye. How the patient angles the device relative to their eye and the central aperture element will determine where the fluid is administered on the eye surface (e.g. on the central cornea or peripheral cornea, or on the conjunctiva). As such, in these embodiments the LED provides for accurate delivery of the liquid formation to a defined location of the ocular surface. Where desired, the illumination source, e.g., LED, reflection on the corneal surface may be employed during administration to accurately deliver the dosage to the ocular surface. In some instances, where the dosage is administered to the ocular surface by administrator other than the patient, e.g., a care giver, the administrator may observe the illumination source as an indication of alignment, and administer the dosage when the observed reflection on the corneal surface indicates alignment. For example, where the illumination source is a provided as a continuous LED ring, or discontinuous pattern, e.g., circle, of distinct LEDs around a mirror, the administrator may observe the reflection of the LED(s) on the corneal surface and determine that the device is aligned with a target ocular location when the pupil is in the center of the observed reflected LED(s). In some such instances, the reflective surface may not be present, and instead just the illumination source is present in the device. Where the dosage is self-administered by the patient, the patient can also employ the reflected LED(s) on the corneal surface as observed by the patient in the reflective surface to similarly determine alignment, e.g., as described in greater detail below.

In some instances, the device includes one or more distance sensors. A distance sensor is a component configured to determine the distance between the device and the target location. Any convenient distance sensor may be present, where such sensors include, but are not limited to, infra-red (IR) sensors, radar sensors, and the like. In some instances where the device includes a distance sensor, the device may further be configured to provide a signal, such as an auditory or visual signal, when the determined distance between the device and the target location is within a predetermined range. For example, the device may be configured to activate an illumination source, e.g., as described above, when the device is within a predetermined range of the target location as determined by the distance sensor. In some instances, the device is configured to be activated when the determined distance between the device and the target location is within a predetermined range. In the above embodiments, the predetermined range may vary, and in some instances is between 1 mm and 250 mm, such as 10 mm to 100 mm.

Figure 500E:
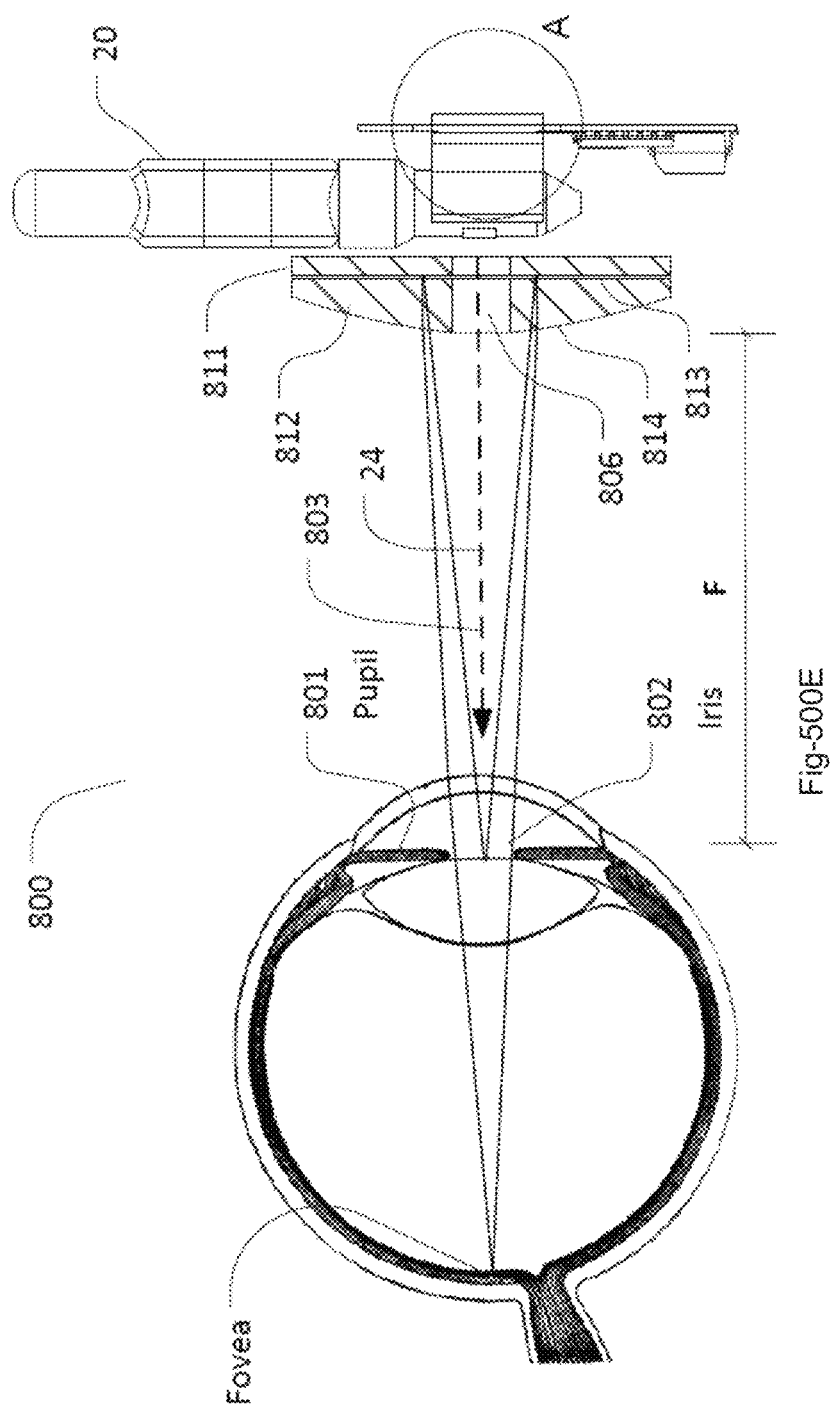
FIG. 500E illustrates another variation of the optical alignment system.

FIG. 500A and FIG. 500B illustrate a device and method for aligning the dispensing stream to the eye of the user in accordance with an embodiment of the invention. Referring to FIG. 500A and FIG. 500B, it can be seen that dispensing device (800) includes a concave mirror (805), such as a spherical mirror having a radius of curvature (R), which defines the position of the focal point (P) at a focal distance (F) as F=R/2 from the mirror surface. The focal plane of the mirror is perpendicular to its optical axis and crosses it at the focal point (P). The mirror (805) may be spherical or aspherical in shape and may be fabricated using any number of materials and techniques. For instance, the mirror (805) may be manufactured from mirrored glass, reflective coatings overlaid upon a substrate, any number of reflective metals, etc. which facilitates removal or cleaning of any ejected fluid which may be deposited upon the mirror (805).

Mirror (805) is positioned in close proximity in front of dispensing ampule (20). Mirror (805) includes a small opening (806) which may be coaxially oriented relative to the stream (24), in one embodiment, for delivery fluid to the eye. While a single opening (806) is shown in this embodiment, multiple openings may be used or defined over the surface of the mirror (805) to accommodate one or more apertures for fluid ejection from the transducer assembly.

In use, the device (800) is aligned to the user eye such that the visible parts of the eye (e.g., cornea, iris, sclera, conjunctiva, etc.) are imaged onto the retina. For the image to be in focus, the mirror (805) should be positioned such that the tissue of interest, e.g., target ocular location, is in the focal plane (or near the focal plane) of the mirror (805). The eye tissue is clearly visible to the user in the reflection from the mirror (805) when the eye is located at the focal plane, e.g., when the distance from the mirror (805) to the tissue of interest, e.g., iris (802), is relatively close to the focal distance (F) of the mirror (805). Such an alignment method helps the user to properly align the dispensing device both in terms of the angle relative to the eye, its lateral position and in terms of setting the distance from the device to the eye. Both are accomplished when the user sees an image of his or her pupil of the eye that includes the target ocular location in the center of the mirror and when such image appears in focus. This alignment mechanism takes advantage of the mirror's natural focal distance and further provides for magnification of the reflected eye so that positioning of the eye relative to the assembly is facilitated, particularly for users whose eyesight may be degraded.

As the radius of curvature of the mirror becomes smaller, the focal point becomes relatively closer to the eye, and the magnification of this imaging system becomes relatively higher. For instance, a flat mirror (one having an infinite radius of curvature) can provide an image only at the distance where the eye can naturally focus onto, which is typically more than about 30 cm from the eye. Due to the double passing of light from the object to the mirror and back to the eye, the minimal distance from the flat mirror to the eye will be about 15 cm. Holding a device so far from the eye will require precise angular alignment to ensure the proper targeting, and also requires the emitted fluid to propagate over a large distance without much divergence. Both of these requirements are hard to meet. Therefore, it is advantageous to use a concave mirror, which places the focal plane closer to the eye. The optimal distance ranges from at a short (first) end defined by the convenience of holding the device without touching the eye lashes, and at a long (second) end defined by the divergence of the emitted fluid, its deviation from the straight line and by the precision of the angular alignment by the user. The latter may be defined as a ratio of the allowable lateral displacement (misalignment) of the emitted fluid divided by the distance between the ejector and the targeted tissue. The closer the device is to the target tissue, the larger is the allowed angle of misalignment, where the emitted fluid will still hit the target area, i.e. the easier it will be for the users to hit the target. In one variation, the optimal range of the distances between the ejector and the targeted tissue (e.g., cornea) is in the range of, e.g., 10-100 mm, such as 20-100 mm, and including 30-60 mm.

As illustrated in FIG. 500A, emitting stream (24) may be coaxial and parallel with the principle axis (803) of the mirror (805) and/or with the central longitudinal axis of the iris (802) or in some offset from the central, visual axis of the iris (802) as illustrated in FIG. 500B. In this embodiment, the fluid ejected through the opening (806) may be emitted in a direction which is parallel relative to the principle axis or to the central longitudinal axis of the iris (802) so that the ejected fluid contacts the eye at a surface region offset from the central axis as well, e.g., cornea, conjunctiva. In yet another alternative shown in FIG. 500C, the ejected fluid (24) may be emitted from the opening (806) which may be centrally located, but the fluid may be emitted at an angle (O) relative to the principle axis of the eye (802).

In another variation, as shown in FIG. 500B, the aperture and opening (806) defined in the mirror (805) may be offset by a distance (807) relative to the principle axis (803). The opening (806) may be accordingly offset by the same distance from the axis (803). The ejected fluid (24) may be emitted towards the targeted region on the eye in a trajectory parallel with the principle axis (803).

In yet another variation, as shown in FIG. 500D, the mirror (805) may entirely omit the opening (806). The fluid delivery assembly may be positioned adjacent to the mirror (805) rather than located behind a proximal surface of the mirror (805), e.g., located behind the mirror (805) relative to the position of the eye when in use. Thus, the aperture of the fluid delivery assembly may be positioned, e.g., above, below, side, etc. relative to the mirror (805) so that the fluid may be emitted from the aperture at an angle (a) relative to the principle axis (803) and towards the targeted region on the surface of the eye.

In yet another variation, as shown in FIG. 4E, the alignment system may include a combination of a mirror (811) and a lens (812) as an alternative to a concave mirror. The mirror (811) may comprise a variety of various reflective materials or surfaces, e.g., a metallic layer, having a flat surface on its reflective side (813). The distal surface of the lens (812), which may also define a flat surface, may be positioned directly against the reflective surface (813) of the mirror (811) and both the mirror (811) and lens (812) may each define one or more openings (806) through which the fluid is delivered. The proximal surface of the lens may be convex (814), as shown. In other variations, fluid delivery assembly may be positioned relative to the mirror (811) and lens (812) assembly as described in other embodiments herein. In use, light may be refracted by the lens (812) and reflected from the mirror (811) in such a way that the front of the eye (iris (802) or conjunctiva or cornea) is imaged onto the retina. In this arrangement, light scattered from the eye passes twice through the lens (812) before and after reflection in the mirror (811).

Regardless of whether the fluid is ejected along the central axis (as shown in FIG. 500A) or offset or at an angle relative to the central axis (as shown in FIG. 500B, FIG. 500C and FIG. 500D), the fluid may be emitted from any number of locations along the mirror (805), adjacent to the mirror (805), or emitted at any number of angles relative to the longitudinal axis of the iris (802) so that the fluid may be directed to contact the surface of the patient's eye at any number of predetermined locations. For instance, the fluid may come from multiple locations, or from multiple apertures from one or more locations over the same or different areas of the mirror, e.g., nasally and temporally at the same time. Additionally, multiple streams of fluid may be emitted simultaneously or serially, or both, if so desired.

In some instances, the optimal focal distance of the mirror (805) ranges, e.g., from 30 mm to 60 mm. Accordingly, in such instances the radius of curvature of the mirror ranges, e.g., from 60 mm to 120 mm, respectively. The diameter of the mirror may be selected such that the image of the iris is easily identified and the pupil is aligned to the center of the mirror. For this purpose, the diameter of the mirror may be slightly larger than a size of the iris and the size may range, e.g., from 15 mm to 30 mm. Alternatively, the diameter of the mirror may be selected so as to provide an image of only a portion of the eye, and in such instances may range from 11 to 15 mm, such as 13 mm.

As illustrated in FIG. 600A, FIG. 600B and FIG. 600C, the mirror (805) may be part of the housing of the device and is made of transparent plastic such as polycarbonate and include a reflective metal layer.

As previously disclosed, the alignment mechanism takes advantage of the mirror's natural focal distance and further provides for magnification of the reflected eye so that positioning of the eye relative to the assembly is facilitated. Size of the image of the eye seen in reflection in the mirror is dependent on the radius of curvature of the mirror (805). The reflection of the eye appears larger to the user viewing the mirror (805) when the radius of curvature of the mirror (805) is smaller and vice versa. An example of this is shown in FIG. 600B and FIG. 600C where the radius of curvature of the mirror (805) in FIG. 600B is, e.g., 60 mm, while the radius of curvature of the mirror in FIG. 600C is, e.g., 30 mm. Consequently, the size of the reflected image appears relatively larger in FIG. 600C. Accordingly, not only the size but the radius of curvature of the mirror may be varied depending upon the desired size of the reflected image.

The mirror (805) may be sized, in one embodiment, to have a circular shape when viewed by the patient so that the reflected image of the patient's eye or iris becomes framed within the mirror (805), as shown in FIG. 600B and FIG. 600C. In other variations, the mirror may be configured to have other shapes when viewed, e.g., elliptical, square, triangular, etc. so long as the eye or iris is visible when properly positioned relative to the assembly. This may be implemented as an indicator to the user that the eye that includes the target location is suitably positioned relative to the opening (806) so that the ejected fluid may be suitably administered to the patient's eye. Additionally, the mirror (805) may also optionally include any configuration of markers or gradations (810), as shown in FIGS. 600B and 6, such as a target or reticle to further facilitate positioning of the patient's iris relative to the assembly. Although the markers or gradations (810) may not be visible to the user as the surface of the mirror may be out of focus, they may be optionally included to facilitate initial positioning relative to the user's eye.

In yet another embodiment, an example of a housing assembly (900) is shown in front and side views of FIG. 700A and FIG. 700B, where a body of the housing (902) may incorporate one or more gripping surfaces (904) upon or around the housing (902). The assembly (900) has a form factor which facilitates the user holding and/or positioning the device relative to the tissue target of interest, such as one or both eyes, by enabling the user to comfortably hold and manipulate the device with a single hand. The housing assembly (900) may accordingly contain and/or enclose the various components of the actuator assembly (906) such as the piezoelectric actuator and actuator controller as well as the ampule, alignment assembly, etc.

With the gripping surfaces (904) thus defined, the one or more apertures through which the fluid is ejected may be positioned in alignment with an opening, slot, or slit (908) defined along the device through which the fluid may pass. Additionally, the assembly may incorporate any of the alignment mechanisms described. In this variation, the alignment mirror (910) is shown to illustrate how such a mechanism may be incorporated into the assembly where the mirror (910) defines the opening, slot, or slit (908) which is in proximity to the one or more apertures. The alignment mirror (910), or any of the other alignment mechanisms, may be incorporated into the assembly (900) and used to enable the user to self-align the one or more apertures to the targeted tissue region and administer fluid delivery for treatment.

As previously described, the size, orientation, and/or location of the one or more apertures may vary. Furthermore, multiple apertures and/or aperture geometries (such as a slit to create a "plane" of fluid) may be optionally incorporated.

The housing (902) may also incorporate an actuator (912), such as a button, switch, or other actuation mechanism to begin the dispensing of the fluid. The actuator (912) is illustrated in this embodiment as a button-type located atop the housing (902) so that the user may depress the actuator (912) during use; however, the actuator (912) may be positioned elsewhere along the housing (902). Additionally, and/or optionally, the aperture (908) may incorporate a shutter or other covering which may open or close when actuated such as by activating the actuator (912).

Another component of the housing assembly (900) may include a cover element (914) which may be moved between a closed and opened position, as indicated by the direction of movement (918) In its closed position, the cover (914) may partially or completely cover or obstruct the alignment mechanism and aperture as well as optionally deactivate the assembly so that fluid is prevented from being dispensed. In its open position, the alignment mechanism and aperture may be unobstructed for use and the assembly may be activated or powered on for dispensing the fluid.

In this variation, the cover element (914) is configured as a sliding cover which may be translated within a channel or groove (916). Sliding the cover into its open position, as shown, exposes the mirror (910), the opening (908) and one or more apertures, and may also power the device on. Sliding the cover into its closed position may slide the cover over the mirror (910), opening (908), and may further deactivate the assembly. While the cover is shown as a sliding mechanism, other variations may incorporate a rotating cover or a cover which may be removed entirely as a separate or coupled structure. Additionally, during use, the cover element (914) may also serve as a thumb-rest, such that the patient uses his/her own thumb as a brace against his/her cheek to stabilize and align the device during use.

Figure 800:
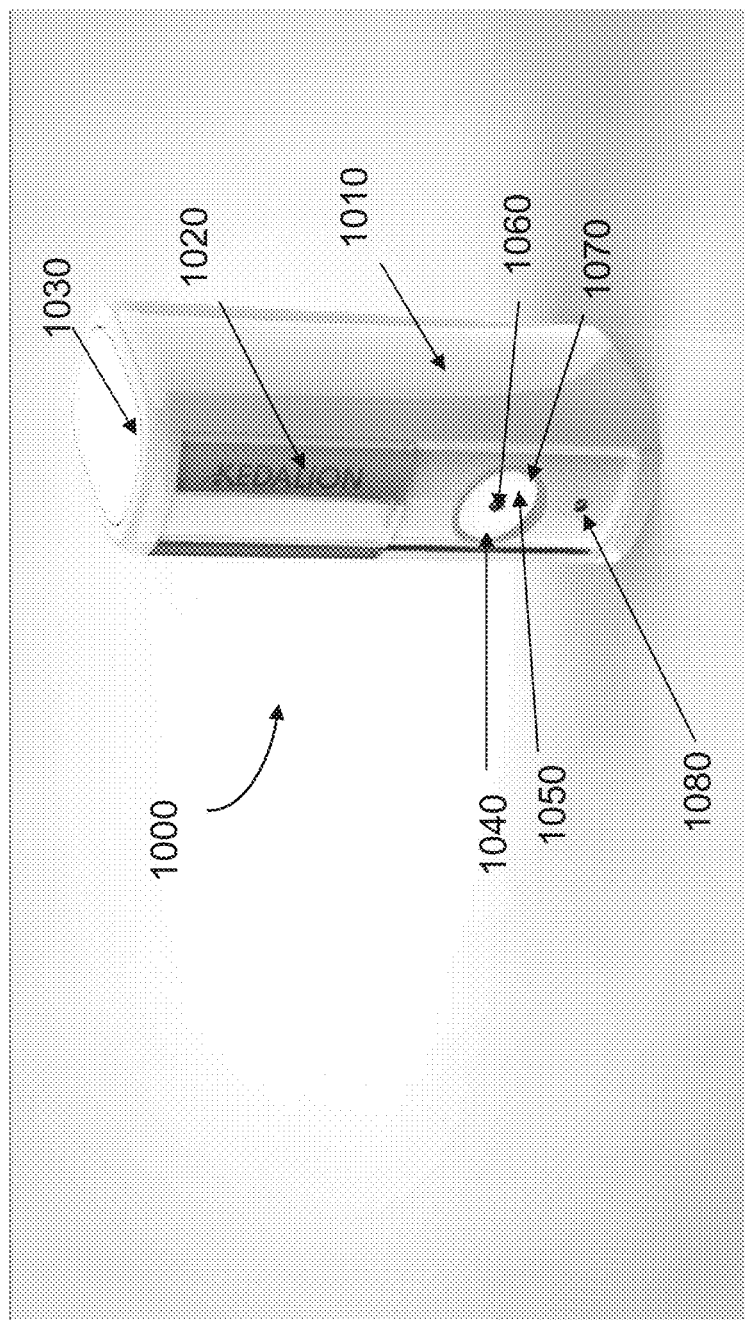
FIG. 800 illustrates another embodiment of a fluid delivery device having a ring LED around a concave mirror and an IR distance sensor.

FIG. 800 provides a view of another embodiment of a fluid delivery device in accordance with the invention. As shown in FIG. 800, device (1000) includes a housing (1010) having a sliding cover (1020). Present in the housing is a fluid delivery package and actuator, e.g., as described above. As shown, the device (1000) includes an actuator button (1030) on the top of the housing. The device also includes a concave-mirror image-based alignment system (1040) as described above, where the concave mirror (1050) includes an opening (1060) through which fluid ejected from the aperture may flow during fluid delivery. Surrounding or bounding the concave mirror (1050) is circular LED (1070), e.g., as described above. Also shown is IR sensor (1080). Further details regarding the handheld device depicted in FIG. 800 are provided in International Application Serial No. PCT/US2018/064529 filed Dec. 7, 2018; the disclosure of which is herein incorporated by reference.

Aspects of the invention further include systems that include a device of the invention, e.g., as described above, or components thereof, in communication with one or more networked devices. As such, systems of the invention may include a delivery device such as described above in communication with a networked device, where the delivery device includes a transmitter, e.g., for communicating with a networked device. A networked device is any device that communicates with at least one other device over a communication link, and in the present invention is a device that includes a communications module that is configured to communicate with the communications module of the delivery device, either directly or via one or more intermediate devices. Networked devices that may be part of a system of the invention may vary, where such devices include, but are not limited to: desktop computing devices, intermediate computing devices, mobile devices (e.g., laptop, cell phone or other mobile computing devices), servers (which may be local or remote), etc. The communication link may vary, where the communication link may be a wired or wireless communication link. Wired communication links may include USB, FireWire, HDMI, Ethernet, LAN, and the like. Wireless communication links that may be employed include, but are not limited to, those employed in any suitable communications network, such as but not limited to wireless personal area networks (WPANs) (e.g., Bluetoooth, ZigBee), wireless local area networks (WLANs) (WiFi), wireless ad hoc networks, wireless metropolitan area networks, wireless wide area networks, cellular networks, global area networks, etc. In such instances, a variety of different types data may be transmitted between the delivery device and the one or more networked devices. Examples of types of data that may be transmitted include, but are not limited to: usage information, such as confirmation that a dose has been delivered, including temporal information, e.g., date and/or time, of dose delivery; information about the status of the device, e.g., number of doses that have been administered, number of doses remaining, operational information about the device (e.g., battery life, functionality, etc.); and the like.

In some aspects, in addition to administration of one or more doses, e.g., micro-doses, the method further comprises the step of measuring efficacy of a given therapy for a condition, e.g., of a disease condition in the subject. In some such instances, the determination is made by comparing the results to the results performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more. The evaluation may vary depending on the nature of the condition being treated. In some embodiments, the subject methods further include diagnosing an individual as having a given condition. Conditions of interest include those further described below.

As used herein, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The above methods find use in a variety of different applications. Certain applications are reviewed in greater detail in the Utility section, below.

Utility

The subject methods and devices find use in a variety of different applications, including treatment applications. The term "treating" or "treatment" as used herein means the treating or treatment of a disease or medical condition in a subject or patient, such as a mammal (such as a human), where the term includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

Presbyopia

An example of a condition that may be treated using methods/devices of the invention is presbyopia. Presbyopia is the impairment of vision due to advancing years or old age and may be characterized by the gradual loss of the ability to focus on nearby objects. Presbyopia may be diagnosed using one or more types of ocular examination procedures, where such examinations may include testing of one or more of visual acuity, e.g., by use of a Snellen chart, Jaeger chart, Rosenbaum chart or ETDRS Near Chart, refraction, binocular vision and accommodation, plus lens to clear near vision, balanced range of accommodation, amplitude of accommodation, crossed cylinder test, accommodative convergence/accommodation, heterophoria and vergence, and vertical imbalance.

In the treatment of presbyopia, the devices and methods may be used to deliver a cholinergic agent, e.g., as described above, to a topical ocular location. As reviewed above, the term "cholinergic agent" refers to any active agent that inhibits, enhances, or mimics the action of the acetylcholine, where cholinergic agents may include both nicotinic and muscarinic classes. Cholinergic agents include agents that modulate the parasympathetic nervous system, i.e., that part of the autonomic nervous system that contracts smooth muscles, dilates blood vessels, increases bodily secretions, and slows the heart rate. In some instances, the cholinergic agent is a miotic agent. Miotic agents are agents that cause contraction of the pupil of the eye. Miotic agents of interest include, but are not limited to, pilocarpine, carbochol, physostigmine, echothiophate, methacholine, moxisylyte and pharmaceutically acceptable salts thereof, and combinations thereof. In some instances, the cholinergic agent is a muscarinic agonist. Muscarinic agonists are agents that activate the activity of a muscarinic acetylcholine receptor, and in some instances the $M_3$ muscarinic receptor subtype. Muscarinic agonists of interest include, but are not limited to: pilocarpine, carbochol, physostigmine, methacholine, acelidine, arecoline, and cevimeline, and pharmaceutically acceptable salts thereof, and combinations thereof. As indicated above, in some instances the cholinergic agent is both a miotic agent and a muscarinic agonist.

When used in the treatment of presbyopia, the methods may result in the improvement of one or more characteristics of presbyopia. For example, methods of the invention may result in a reduction in pupil diameter as compared with reduction in pupil diameter observed prior to cholinergic agent administration. The magnitude of the reduction may vary, and in some instances may range from 0.25 to 10 mm, such as 1 to 9 mm, including 2 to 8 mm, where in some instances the reduction ranges from 0.25 to 3.0 mm, such as 0.5 to 1.5 mm, including 0.5 to 1.0 mm. In some instances, the methods may result in an improvement in uncorrected near visual acuity or other measures of visual function including uncorrected intermediate or distance vision, contrast sensitivity or depth of focus, amongst other measures. Where visual acuity is measured using a chart, such as a Jaeger or Rosenbaum near card, Snellen card or ETDRS Near Chart, the methods may result in an improvement of one or more lines on the chart, such as 1 to 8 lines, including 2 to 6 lines. In some instances, magnitude of improvement with respect to a letter than can be read at 20 feet is 5 feet or more, such as 10 feet or more, including 15 fee or more, where the magnitude ranges in some instances from 5 to 60 feet, such as 5 to 30 feet, e.g., 10 to 25 feet, including 15 feet, e.g., where visual acuity improves from 20/40 to 20/25 or 20/20.

When used in the treatment of presbyopia, the methods of the invention in which a micro-dose is delivered to a topical ocular location may result in at least a reduction, if not substantial or complete elimination, of one or more adverse effects of the administered active agent, such as but not limited to: temporary irritation/burning/stinging of the eye, ocular inflammation, ciliary spasm, temporary blurred vision, poor vision in dim light, headache, brow ache, etc.

Dry Eye Disease An example of another condition that may be treated using methods/devices of the invention to deliver a cholinergic agent is dry eye disease. Keratoconjunctivitis sicca (KCS), also called keratitis sicca, sicca syndrome, xerophthalmia, dry eye syndrome (DES), or simply dry eyes, is an eye disease caused by decreased tear production, increased tear film evaporation, or Meibomian gland dysfunction, commonly found in humans, most often post-menopausal females, and some animals. Typical symptoms of keratoconjunctivitis are dryness, burning and a sandy, gritty eye irritation that gets worse as the day goes on. Keratoconjunctivitis sicca is characterized by inadequate tear film protection of the cornea because of either inadequate tear production or abnormal tear film constitution, which results in excessively fast evaporation or premature destruction of the tear film. The tear film is constituted by 3 layers: (1) a lipid layer, produced by the Meibomian glands; (2) an aqueous layer, produced by the main and accessory lacrimal glands; and (3) a hydrophilic mucin layer, produced by the conjunctival goblet cells. Any abnormality of 1 of the 3 layers produces an unstable tear film and symptoms of keratitis sicca. Keratoconjunctivitis sicca can also be caused by abnormal tear composition resulting in rapid evaporation or premature destruction of the tears. When caused by rapid evaporation, it is termed evaporative dry eyes. In this, although the tear gland produces a sufficient amount of tears, the rate of evaporation of the tears is too rapid. There is a loss of water from the tears that results in tears that are too "salty" or hypertonic. As a result, the entire conjunctiva and cornea cannot be kept covered with a complete layer of tears during certain activities or in certain environments.

In embodiments where the methods and devices are used in treating dry eye disease, the delivered micro-dose may include a cholinergic agent, e.g., as described above, effective to reduce the intraocular pressure so as to treat the subject for the dry eye disease. In addition or alternatively, in treating dry eye the delivered micro-dose may include an anti-inflammatory/immunomodulatory/immunosuppressive agent, e.g. a Cyclosporine, such as Cyclosporine A and derivatives thereof; FK-506, Rapamycin, Buspirone, Spiperone, and/or their derivatives, etc. In one such embodiment, the administered micro-dose is an emulsion including water, a hydrophobic component and a cyclosporin component, e.g, such as described in U.S. Pat. Nos. 8,629,111; 8,633, 162; 8,642,556; 8,648,048; 8,685,930; and 9,248,191; the disclosures of which are herein incorporated by reference, e.g., Restasis® Cyclosporine ophthalmic emulsion. In some embodiments, the active agent administered by micro-dose is an anti-inflammatory agent, such as lifitegrast, e.g., as described in U.S. Pat. Nos. 7,314,938; 7,745,460; 7,790, 743; 7,928,122; 8,048,047; 8,168,655; 8,367,701; 8,592, 450; 8,927,574; 9,085,553; 9,216,174; 9,353,088; 9,447, 077; 9,890,141 and 10,124,000; the disclosures of which are herein incorporated by reference, e.g., Xiidra lifitegrast ophthalmic solution. In some instances, the micro-dose includes a steroid active agent, such as Corticosteroids, such as Prednisolone, Prednisolon, Dexamethasone, Loteprednol, Difluprednate, Fluorometholone, Rimexolone and Medrysone, etc. In some instances, the micro-dose is a micro-dose of an artificial tears, including low and high viscosity artificial tears, where artificial tears include ophthalmic formulations containing carboxymethyl cellulose, polyvinyl alcohol, hydroxypropyl methylcellulose (a.k.a. HPMC or hypromellose), hydroxypropyl cellulose and hyaluronic acid (a.k.a. hyaluronan, HA), etc, where compositions may further contain water, salts and polymers but lack the proteins found in natural tears. Where the delivery formulation is highly viscous, devices as describe herein may be particularly suited for delivery of such formulations, as the orifice of the device may be sized to avoid clogging of the orifice by the highly viscous formulation.

The methods may result in improvement of one or more symptoms of the dry eye disease, which symptoms may include, but are not limited to: foreign body sensation or irritation, staining of the ocular surface/epithelium with sodium fluorescein or rose bengal, deficiency of tears (aqueous deficiency) (as measured by Schirmer's testing), reduced vision, reduced tear break up time, reflex tearing, increased osmolarity of the tear film, meibomian gland dysfunction, conjunctival redness/injection staining of the ocular surface with lisamine green, etc.

When used in the treatment of dry eye, the methods of the invention in which a micro-dose is delivered to a topical ocular location may result in at least a reduction, if not substantial or complete elimination, of one or more adverse effects of the administered active agent, such as but not limited to: eye burning, redness, tearing, discharge, pain, itching, stinging, visual blurring, feeling as if something is in the eye. conjunctival hyperemia, headache, increased lacrimation, eye pruritus and sinusitis, etc.

Sjogren's Syndrome

An example of another condition that may be treated using methods/devices of the invention to deliver a cholinergic agent is Sjogren's syndrome. Sjogren's syndrome and autoimmune diseases associated with Sjogren's syndrome are also conditions associated with aqueous tear deficiency. Drugs such as isotretinoin, sedatives, diuretics, tricyclic antidepressants, antihypertensives, oral contraceptives, antihistamines, nasal decongestants, beta-blockers, phenothiazines, atropine, and pain-relieving opiates such as morphine can cause or worsen this condition. Infiltration of the lacrimal glands by sarcoidosis or tumors, or post-radiation fibrosis of the lacrimal glands can also cause this condition. In embodiments where the methods and devices are used in treating Sjogren's syndrome, the delivered micro-dose may include a cholinergic agent, e.g., as described above, effective to reduce the intraocular pressure so as to treat the subject for Sjogren's syndrome.

Other conditions include, but are not limited to, those characterized by miscellaneous refractive errors, including hyperopia, astigmatism, post-surgical optical aberrations, e.g., following cataract surgery, LASIK, PRK, corneal transplantation etc., as well as other conditions where a pinhole effect may be beneficial with respect to the condition.

Glaucoma

An example of another condition that may be treated using methods/devices of the invention is glaucoma. Glaucoma is a collection of disorders characterized by progressive visual field loss due to optic nerve damage. It is the leading cause of blindness in the United States, affecting 1-2% of individuals aged 60 and over. Although there are many risk factors associated with the development of glaucoma (age, race, myopia, family history, and injury), elevated intraocular pressure, also known as ocular hypertension, is the only risk factor successfully manipulated and correlated with the reduction of glaucomatous optic neuropathy. In glaucoma associated with an elevation in eye pressure the source of resistance to outflow is in the trabecular meshwork. The tissue of the trabecular meshwork allows the "aqueous" to enter Schlemm's canal, which then empties into aqueous collector channels in the posterior wall of Schlemm's canal and then into aqueous veins. The aqueous or aqueous humor is a transparent liquid that fills the region between the cornea at the front of the eye and the lens. The aqueous humor is constantly secreted by the ciliary body around the lens, so there is a continuous flow of the aqueous humor from the ciliary body to the eye's front chamber. The eye's pressure is determined by a balance between the production of aqueous and its exit through the trabecular meshwork (major route) or via uveal scleral outflow (minor route). The trabecular meshwork is located between the outer rim of the iris and the internal periphery of the cornea. The portion of the trabecular meshwork adjacent to Schlemm's canal causes most of the resistance to aqueous outflow (juxtacanalicular meshwork) In embodiments where the methods and devices are used in treating glaucoma, the delivered micro-dose may include a cholinergic agent, e.g., as described above, effective to reduce the intraocular pressure so as to treat the subject for the glaucoma. In some instances, the glaucoma is angle-closure glaucoma. In some instances, the condition is acute angle-closure glaucoma and in other instances, the condition is chronic angle-closure glaucoma".

In treating glaucoma. in some instances the ophthalmic agent is a cholinergic agent, e.g., as described above. Also of interest in treating glaucoma is the use of intraocular pressure modulatory agents. such that in some instances the methods/devices of the invention deliver an intraocular pressure modulatory agent to treat glaucoma. An "intraocular pressure modulatory agent" can comprise a drug and may be any of the following or their equivalents, derivatives or analogs: agents that work to increase the outflow of fluid (aqueous humor) from the eye, e.g., prostaglandin active agent, such as prostaglandin analogues, such as bimatoprost, travoprost, tafluprost, latanoprost, etc., including Xalatan® (latanoprost), Lumigan® (bimatoprost), Travatan Z® (Travoprost), and Zioptan™ (tafluprost), and Vyzulta™ (latanoprostene bunod); agents that work to decrease fluid (aqueous humore) production, e.g., beta blockers, such as timolol, betaxolol, levobunolol, atenolol (e.g., as described in U.S. Pat. No. 4,952,581); agents that work to both decrease fluid production and increase drainage, e.g., alpha agonists, such as apraclonidine or brimonidine (e.g., as described in U.S. Pat. No. 5,811,443) e.g., Alphagan®P (brimonidine), Iopidine®; agents that decrease production of intraocular fluid, e.g., carbonic anhydrase inhibitors (CAIs), e.g., acetazolamide, dorzolamide, brinzolamide, methazolamide, dichlorphenamide, diamox, and the like, such as Trusopt® (dorzolamide), Azopt® (brinzolamide), etc.; agents that increase the drainage of fluid, such as Rho kinase inhibitors, e.g., Rhopressa® (netarsudil); and combination therapies, e.g., Cosopt® (a combination of a beta blocker (timolol) and a carbonic anhydrase inhibitor (dorzolamide)) and a preservative-free formulation thereof (Cosopt® PF); Combigan® (a combination of an alpha agonist (brimonidine) with a beta blocker (timolol); and Simbrinza® (a beta blocker-free combination medication consisting of brinzolamide and brimonidine); etc. In some instances, the therapeutic agent is already marketed for glaucoma, and commercially available preparations thereof can be used.

When used in the treatment of glaucoma, the methods of the invention in which a micro-dose is delivered to a topical ocular location may result in at least a reduction, if not substantial or complete elimination, of one or more adverse effects of the administered active agent, such as but not limited to: change in iris color and growth of eyelashes, blurred vision, double vision, drooping eyelid, burning or stinging in your eye, eye itching or redness, watery eyes, feeling as if something is in the eye, headache, weakness, drowsiness, numbness, tingling, cold feeling in your hands or feet, ringing in ears, dry mouth, nausea, diarrhea, loss of appetite, upset stomach, skin rash or worsening psoriasis, sleep problems (insomnia), cough, stuffy nose, bradycardia, exacerbation of asthma, eye redness, corneal abnormalities, instillation site pain, burst blood vessels in the eye, eyelid skin darkening, browning of the iris, increased sensitivity to light, oozing or eye discharge, fat atrophy, etc.

Myopia

Aspects of the invention also include treatment and/or prevention of myopia. Myopia is the condition known as "near-sightedness", where the image in front of the eye is focused in front of the retina rather than exactly on the retina. This focus of the image on the retina is also referred to as "emmetropia". The image in myopia may be focused in front of the retina for one or both of the following reasons: either the refractive strength of the front of the eye at the cornea and lens is excessive; and/or the axial length of the eye is too long, such that the retina is posterior to the image focal point, causing blurred vision. To counteract this visual blurring, those affected move closer to the object to be viewed. This moves the focal point of the image back and closer to the retina, causing the vision to become more clear.

Methods of the invention may be employed prevent the occurrence of myopia, or modulate, such as inhibit or slow down, the progression of myopia.

In such instances, anti-cholinergic agents, including both long acting and short acting agents (e.g., atropine, tropicamide, etc.), such as described above, may be administered to the subject.

When used in the treatment of myopia, the methods of the invention in which a micro-dose is delivered to a topical ocular location may result in at least a reduction, if not substantial or complete elimination, of one or more adverse effects of the administered active agent, such as but not limited to: eye pain and stinging, blurred vision, photophobia, superficial keratitis, decreased lacrimation, etc.

Other Disease Conditions

Other disease conditions that may be treated by methods and devices of the invention include, but are not limited to, those described in U.S. Pub. 2017/0344714 and U.S. Pat. No. 9,087,145 the disclosures of which are herein incorporated by reference.

Diagnostic/Examination Applications

Diagnostic/examination applications include, but are not limited to, mydriasis applications where the pupil is dilated, e.g., to permit examination of the retina and other deep structures of the eye. Mydriatic agents that may be employed in such applications include, but are not limited to: atropine, atropine sulfate, atropine hydrochloride, atropine methylbromide, atropine methylnitrate, atropine hyperduric, atropine N-oxide, phenylephrine, phenylephrine hydrochloride, hydroxyamphetamine, hydroxyamphetamine hydrobromide, hydroxyamphetamine hydrochloride, hydroxyamphetamine iodide, cyclopentolate, cyclopentolate hydrochloride, homatropine, homatropine hydrobromide, homatropine hydrochloride, homatropine methylbromide, scopolamine, scopolamine hydrobromide, scopolamine hydrochloride, scopolamine methylbromide, scopolamine methylnitrate, scopolamine N-oxide, tropicamide, tropicamide hydrobromide, and tropicamide hydrochloride.

Kits

Also provided are kits that find use in practicing embodiments of the methods, such as those described as described above. The term "kit" refers to a packaged delivery device or component thereof, e.g., ampule, such as described above. In addition to the above-mentioned components, kits may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXAMPLES

I. Treatment of Presbyopia

A 10 µl micro-dose of a 1% pilocarpine solution was self-administered using an electromagnetic actuated fluid delivery device, e.g., as described above, by three subjects to their own eye. The age range of the subjects was 52 years to 68 years, and all subjects were male. The pilocarpine micro-dose was self-administered by the subjects.

Baseline, pre-dose values of pupil diameter and near visual acuity in both eyes prior to dosing was measured for all subjects, and then following the baseline measurements, the subjects were dosed in only one eye (the eye with the poorer visual acuity) with the micro-dose pilocarpine solution. Approximately 45 to 60 minutes after dosing, pupil diameter and near visual acuity were again tested. Near visual acuity was measured using a Snellen card at a distance of 40 cm. A tabulation of results is given below in Table A.

TABLE A

| Subject 1-3 | mean | SD |
| --- | --- | --- |
| Mean Age (yrs) | 58.3 | 8.5 |
| Mean baseline pupil dia dosed eye (mm) | 2.9 | 0.62 |
| Mean baseline pupil dia non-dosed eye (mm) | 2.8 | 0.9 |
| Median baseline near visual acuity | 20/30 | n/a |
| Mean post-dose pupil dia (mm) | 2.2 | 0.81 |
| Mean change in dosed pupil dia (mm) | −0.7 | 0.2 |
| Mean non-dose pupil dia (mm) | 3.0 | 0.6 |
| Mean change in non-dosed pupil dia (mm) | 0.2 | 0.5 |
| Median dosed eye near visual acuity | 20/20 | n/a |
| # of lines change in visual acuity | 2 | 1 |

As can be seen in the data summary, the non-dosed eye experienced no miotic effect, there was no reduction in pupil diameter. The dosed eye experienced a substantial miotic effect in all subjects with a mean reduction in pupil diameter of 0.70 mm (range 0.43 to 0.80 mm). Additionally, the dosed eye experienced a substantial improvement in near visual acuity in all subjects with a mean improvement of 2 lines (range 1 to 3 lines).

II. Treatment of Glaucoma

A. Introduction

Glaucoma affects over 60 million people globally and is the second leading cause of blindness. It has been estimated that nearly 3 million people have glaucoma in the United States alone. Topical ocular medical therapy has been and continues to be essential for the control of intraocular pressure (IOP), a major risk factor for the development of optic neuropathy. Over the past three decades, difficulty with self-administration of eye drops has been well documented in the clinical literature, many of whom are patients with glaucoma or ocular hypertension (OHT). Problems that are reported with high prevalence for self-administration include missing the eye due to poor technique, and contamination resulting from touching the bottle tip to the eye. In addition, several of the studies report a mismatch between patient self-perceptions of eye drop technique and actual, objective measures of proper administration. This is particularly problematic for patients with glaucoma or ocular hypertension who must use eye drops successfully every day to comply with their prescribed therapy.

For practical reasons, eye drop bottles are designed to allow patients to self-administer with relatively minimal force. In order to achieve this, the orifice diameter is fairly large. However, this leads to increased drop volumes, which is currently estimated to be approximately 30-50 µl per drop from existing topical delivery bottles. Not only is this more than the required therapeutic dose, it also is more than can be held physically in the ocular cul de sac. In addition, the excess volume may drain into the nasolacrimal system, flood the lower eyelid margin or elicit a strong eye blink reaction which can force fluid from the eye surface and may contribute to more side effects.

B. AcuStream™ Device

The AcuStream™ topical ocular drug delivery device prototype employed in this study was developed by Kedalion Therapeutics (Menlo Park, CA) to overcome compliance and dosing adherence obstacles related to self-administration with standard eye drop delivery. Standard drop volume doses can vary from 30-50 µl while the AcuStream™ device delivers a dose volume of approximately 10 µl, corresponding to the fluid volume capacity of the eye surface. The AcuStream™ device consists of a disposable and sterile drug-filled ampule, a piezoelectric actuator, and a handheld apparatus which houses a battery-powered printed circuit board, e.g., as further described above. When actuated, the device emits a low impact, collimated liquid dose to the surface of the eye. The device is designed to overcome the obstacles presented by patient self-administered drug therapy using standard eye dropper bottles. As mentioned above, the AcuStream™ device is designed to deliver a dose of approximately 10 µl which is believed to be sufficient to achieve an equivalent therapeutic effect when compared with standard eye drop instillation. The low impact drug stream is collimated and intended to deposit the dose to the area between the upper and lower eyelids at an impact velocity believed to be lower than the threshold to initiate a blink reaction. The patient's head is comfortably positioned with the eyes facing straight ahead instead of with the head extended backward as with eye drops. The AcuStream™ device's piezoelectric actuator is intended to replace the variable squeeze force required for standard eye drop administration.

C. Pupil Dilation Using Tropicamide & Phenylephrine

1. Objective:

Trial 1 compared the safety, efficacy (dose volume equivalence), and comfort associated with AcuStream (pre-trial calibration volume=9.2 µl) versus the standard eye dropper (approximate dose volume=30 µl) on patient volunteers requiring pupil dilation for subsequent retinal examination using a combination formulation of 1% w/v tropicamide and 2.5% w/v phenylephrine to induce mydriasis.

2 Method:

a. Study Population: The study population consisted of 20 male and female patients, age 21 years or greater (Table 1), selected from those attending the daily retina clinic and all requiring bilateral pupil dilation fundus for later fundus examination by means of indirect ophthalmoscopy.

TABLE 1

Trial 1 Population Demographics for
Post-Instillation Measurement

| | VALUE |
| --- | --- |
| Total # of Patients | 20* |
| Female | 12 (60%) |
| Male | 7 (35%) |
| Age (Mean) | 57.5 |
| Std Dev | 19.37 |
| Std Error | 4.44 |
| Median | 65.0 |
| Q1, Q3 | 40.0, 72.0 |
| Min, Max | 21, 86 |

*Age and gender were not recorded for one patient

All patients were advised of the study details and signed informed consent documents in accordance with the Declaration of Helsinki to confirm agreement to participate. Patients who showed evidence of corneal opacities that could interfere with accurate pupil measurements, pupillary defects, anterior chamber synechiae, or who experienced recent trauma or were diagnosed with diabetic retinopathy were excluded. Patients were also excluded if their baseline pupil diameter exceeded 4.0 mm or had a history of open or closed angle glaucoma. After screening, patients were instructed to remain in the clinic area for a period of 3 hours for pupil dilation measurements taken at 30-minute intervals.

b Study Design:

An acute prospective, randomized, actively controlled and masked examiner design comparison of AcuStream™ device delivery of a combination formulation of 2.5% w/v phenylephrine and 1.0% w/v tropicamide with a single drop (via standard dropper) consisting of the same formulation for pupil dilation was employed for this study. Each patient's eyes were randomized by means of a random numbers table; an odd number dictated that the patient's right eye (OD) was assigned the "test" (AcuStream™) eye, while an even number meant that the patient's left eye (OS) was the test eye. The contralateral eye served as the control eye (standard eye dropper administration).

c. Procedure:

All patients were seated comfortably while undergoing slit lamp examination of the anterior chamber and fluorescein staining under blue light illumination. Magnified digital images from a slit lamp mounted camera were obtained for both eyes as a baseline indicator of corneal epithelial integrity and used for subsequent post treatment comparison. The baseline pupil diameters for each eye were measured by a sole masked examiner utilizing the automated Neurotech 3000 Pupillometer (Neurotech, Inc.) with an empirically determined accuracy of +0.3 mm. The ambient lighting level was set at 50 mW/cm$^2$ and stray light was minimized through the use of device mounted eyecup resting firmly, but comfortably, at the eye orbit margins. The eyecup stabilized the device position and maintained a constant vertex distance. The pupil diameter was measured continuously for 5 sec with the result averaged over that time interval and immediately recorded.

The mydriatic formulation was administered by a sole ophthalmologist to each eye and digitally recorded via GoPro 5 for later comparison analysis. Patients were requested to look up slightly because the ophthalmologist was standing and directed an AcuStream™ dose to the inferior conjunctiva of the test eye and a single standard drop dose to the inferior conjunctiva/lower lid sulcus of the control eye.

Pupil diameters were measured for each patient at 30, 60, 90, 120, 150 and 180 minutes after dose instillation. After the final measurement, patients underwent re-examination and fluorescein staining at the slit lamp noting any drug delivery related disruption to the corneal surface (Table 2).

TABLE 2

Measurement Schedule for Trial 1

| Type of examination | Pre-instil-lation (Baseline) | Post-Instil-lation (t = 0 min) | Final post-treatment slit lamp exam | Post-instillation (t = 30, 60, 90, 120 minutes) |
|---|---|---|---|---|
| Fluorescein staining | x | | x | |
| Slit amp exam | x | | x | |
| Pupillometry | x | | | x |
| Patient visual analogue comfort scale | | x | | |

A patient Analog Visual Comfort Scale (FIG. 1500) was also administered within 5 minutes of drug instillation in order to compare their perception of comfort associated with the two modes of topical delivery. Patients were asked to indicate their level of comfort during drug administration for each eye on the linear scale shown below and served as the metric for later comparison.

Figure 900B:
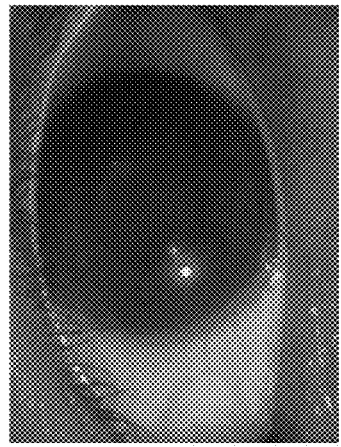
Figure 900A:
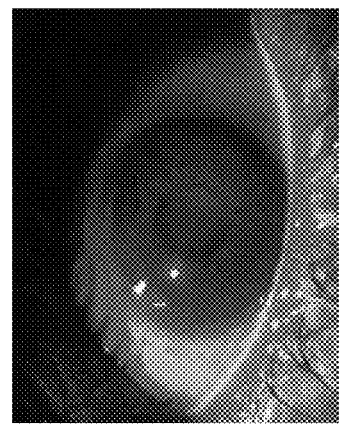

3. Results:

a. Safety: The safety of the two delivery methods were compared by means of a slit lamp examination (Haag-Streit 900BQ slit lamp) of the corneal surface and anterior chamber prior to drug delivery and after the 120-minute pupil diameter measurement. Fluorescein staining and blue light illumination of the eye was similarly employed as a sensitive indicator of epithelial integrity. No areas of epithelial damage were observed under slit lamp illumination or under blue light illumination. Digital images were obtained for both eyes of each patient under slit lamp illumination (FIG. 900A-Right eye, pre-dosing, AcuStream™, FIG. 900B-Left eye, post-treatment, standard dropper). There was no evidence of corneal epithelial disruption and no adverse events or complications were observed.

b. Pupillometry:

Post-instillation pupillometry was conducted at 30-minute intervals up to three hours by a sole examiner who was blinded to the randomization conditions. At the 90-minute time point, mean pupil diameters had increased from 3.34 mm to 6.95 mm for the "test" eyes and 3.35 mm to 7.26 mm for control (FIG. 1000). The pupil diameter increase was statistically significant for both treatment conditions (Wilcoxon signed rank test $p<0.005$) and was sustained for 180 minutes post-instillation (see FIG. 1100).

The mean pupil diameter difference between test and control eyes at baseline and at all post instillation time points was found to be statistically insignificant at all time points. At the final post-instillation time point, there continued to be no significant difference between test and control eyes (FIG. 1200).

c. Comfort:

Within five minutes after drug administration, patients were instructed through a Spanish-speaking translator and a trained ophthalmologist to place a mark along the visual analog comfort scale indicating their degree of comfort for each eye. A score of 0 reflects "least comfortable", while a score of 100 indicated "most comfortable". The line was exactly 100 mm long, enabling the generation of a numerical value to represent their feeling of comfort.

The average visual analog comfort scale averaged 81.7 mm for AcuStream™ treated eyes versus 58.7 mm for standard drop treated eyes (refer to Table 3). Based on the average difference in scores between eyes it was determined that AcuStream™ delivery was 39% more comfortable than standard eye drop delivery and that this difference was statistically significant (Wilcoxon Signed Rank test-exact, P=0.0190).

TABLE 3

Visual Analog Comfort Scale Data Summary

| POPULATION | TEST GROUP | CONTROL GROUP |
|---|---|---|
| N | 19 | 19 |
| Mean | 81.7 | 58.7 |
| Std Dev | 24.06 | 36.76 |
| Std Error | 5.52 | 8.43 |
| Median | 92.0 | 60.0 |

DIFFERENCE IN POST-INSTILLATION PVACS (TEST-CONTROL), mm *

| | |
|---|---|
| N | 19 |
| Mean * | 23.0 |
| Std Dev | 38.97 |
| Std Error | 8.94 |
| Median | 0.0 |
| Q1, Q3 | 0.0, 5.0 |
| Min, Max | −50, 100 |

* Calculated as the mean of individual differences

The feeling of comfort or pain may be influenced by many factors. For the present study the factors identified included a stinging sensation elicited by the mydriatic formulation during impact of the microfluidic stream or drop. However, review of the videos obtained during administration revealed observable body reactions, such as forced blink reaction, eyelids remaining closed after administration, turning the head, shaking the head or leaning to one side. These reactions were more pronounced in the standard drop delivery group.

4. Summary a Method:

Twenty (20) patients were recruited for Trial 1. For each patient, drug was administered to one eye using AcuStream™ ("test") or standard eye drops ("control") and the other eye the other method. Eye selection for treatment type was randomized and blinded. Pupil diameters at baseline and subsequent time points were measured by means of slit lamp examination and fluorescein staining prior to and after drug administration for both delivery methods. Post-instillation pupil measurements were repeated at 30-minute intervals over a period of two hours by a sole examiner with no prior knowledge of the randomization conditions.

b. Results:

There was no evidence of corneal epithelial disruption or adverse events associated with either mode of administration. Mean pupil diameters increased from 3.34 mm to 6.95 mm for the AcuStream™ treated eyes, and increased from 3.35 mm to 7.26 mm for the standard drop delivery at 90 minutes post-administration. The pupil diameter increase was statistically significant for both treatment conditions (Wilcoxon Signed Rank test p<0.0001). The mean pupil diameter difference between treatment conditions was found to be statistically non-significant at all post instillation time points.

Comfort was assessed by means of an ocular comfort scale for both test and control eyes. The patient comfort score was 39% greater for AcuStream™ than for the standard eye drops. Based on video analysis, the sensation of "stinging" from the tropicamide/phenylephrine formulation was judged to be demonstrably less for the AcuStream™ treated eyes.

D. Intraocular Pressure Reduction with Latanoprost

1. Objective:

Trial 2 compared the efficacy (dose volume equivalence) of 0.005% w/v latanoprost for intraocular pressure reduction when delivered via AcuStream™ (pre-trial calibration volume=9.2 μl) versus the standard eye dropper for topical drug delivery (approximate volume=30 μl).

2. Method:

a. Study Population:

Patients included in Trial 2 have previously been diagnosed with primary open angle glaucoma on the basis of intraocular pressure and visual field testing, fundus examination or optical coherence tomography (OCT) data and are currently on prostaglandin analog medical therapy. Patients with corneal abnormalities that would interfere with accurate IOP measurements with applanation tonometry, use of an oral or topical ophthalmic steroids within the past 14 days from screening date, any active ocular surface or anterior segment disease, or progressive field loss during the past year were excluded from the study. Thirteen men and five women participated in the trial.

Recruited patients were taken off medical therapy for a period of 3-4 weeks prior to the study to allow drug "wash out", thereby elevating their IOPs to pre-treatment levels which was confirmed by examination of the patients' chart history. Patients were randomly assigned as "test" (AcuStream™), or "control" (standard eye dropper). The mean age of the control group and test group were 61.0 years and 65.2 years, respectively. Table 4 summarizes the patient demographics for this trial.

TABLE 4

Patient Demographics for Trial 2

| | TEST (ACUSTREAM) | CONTROL (EYE DROPPER) | OVERALL |
|---|---|---|---|
| Total N | 9 | 9 | 18 |
| Female | 7 (77.8%) | 6 (66.7%) | 13 (72.2%) |
| Male | 2 (22.2%) | 3 (33.3%) | 5 (27.8%) |
| Age (Mean) | 61.0 | 65.2 | 63.1 |
| Std Dev | 9.90 | 4.47 | 7.76 |
| Std Error | 3.30 | 1.49 | 1.83 |
| Median | 61.0 | 65.0 | 64.0 |
| Q1, Q3 | 56.0, 65.0 | 62.0, 69.0 | 59.0, 69.0 |
| Min, Max | 45.0, 76.0 | 58.0, 70.0 | 45.0, 76.0 | b. Study Design:

Trial 2 was an acute prospective, randomized, actively controlled and masked examiner design comparison of 0.005% w/v latanoprost delivered via AcuStream™ (pre-trial calibration volume=9.2 μl) or a standard eye dropper (approximate dose volume=30 μl) for acute IOP reduction. The patients assigned to either the "test" or "control" group by means of a random numbers table in order to mitigate any potential cross-over effects that could confound data interpretation. An odd number dictated that the patient was in the test group, while even-numbered patients were in the control group.

c. Procedure:

After performing slit lamp examinations on each patient to verify eligibility and obtaining informed consent, intraocular pressure (IOP) was measured by a sole experienced examiner who was blind to the randomized conditions. A pre-calibrated Goldmann applanation tonometer coupled to a Haag-Streit 900 EQ slit lamp was used to conduct baseline IOP measurements. Once baseline IOP data were verified to be equivalent to pre-medical therapy levels (based on patient's treatment history), the patient then continued to the dosing stage of the study.

Latanoprost solution was administered by a sole ophthalmologist to both eyes of each patient, based on the pre-determined randomized condition. As in Trial 1, patients were requested to look up slightly because the ophthalmologist was standing as either an AcuStream™ dose was directed to the inferior conjunctiva or a single standard drop dose was administered to the inferior conjunctiva/lower lid sulcus of the patient's eyes.

3. Results:

The average baseline IOP for the AcuStream™ group (9 patients, N=18 eyes) was 18.6 mm Hg and 17.7 mm Hg for the standard dropper group (9 patients, N=18 eyes). IOPs were at approximately 8 hours after dosing and decreased to 13.6 mm Hg for the test group and 13.3 mm Hg for the standard drop group. The average decrease measured per patient was 5.0 mm Hg for the test group and 4.3 mm Hg for the control group (FIG. 1300). Table 5 summarizes the results:

TABLE 5

Trial 2 Results, Pre- and Post-Treatment

|  | TEST | CONTROL |
| --- | --- | --- |
| PRE-TREATMENT IOP |  |  |
| N | 18 | 18 |
| Mean | 18.6 | 17.7 |
| Std Dev | 2.71 | 4.12 |
| Std Error | 0.64 | 0.97 |
| Median | 18.0 | 18.0 |
| POST-TREATMENT IOP |  |  |
| N | 18 | 18 |
| Mean | 13.6 | 13.3 |
| Std Dev | 2.94 | 3.94 |
| Std Error | 0.69 | 0.93 |
| Median | 13.0 | 12.0 |
| TOTAL PRESSURE REDUCTION |  |  |
| N | 18 | 18 |
| Mean | −5.0 | −4.3 |
| Std Dev | 1.75 | 3.25 |
| Std Error | 0.41 | 0.77 |
| Median | −5.0 | −4.0 |

The data were plotted graphically and revealed a large range of IOP reduction for the control group. This can be attributed to a single patient outlier with a measured baseline IOP (OD) of 30 mm Hg and a post-instillation IOP of 17 mm Hg. (See FIG. 1400) There was a statistically significant decrease in IOP between baseline and post treatment measurements (Student' T-test p<0.001), and no statistically significant differences in baseline IOP or IOP reduction between groups (Wilcoxon Ranked Sum test, p=0.3447).

4. Summary a. Method: Eighteen (18) patients previously diagnosed with glaucoma and currently on prostaglandin analog medical therapy were identified and had consented to participate in Trial 2. Each patient was randomized into either a test cohort (AcuStream™) or a control cohort (standard eye dropper), so that both eyes of a patient were treated with the same delivery method. IOP was measured by a sole experienced examiner blinded to the randomization conditions using a pre-calibrated Goldmann applanation tonometer.

b. Results: IOP baselines were established and conformed to pre-medical therapy levels based on pre-study history. The average baseline IOP for the "test" group averaged 18.6 mm Hg while the "control" group averaged 17.7 mm Hg. Post-treatment IOP measurements were taken approximately 8 hours after dosing, and decreased in both groups to 13.6 mm Hg for the AcuStream™ treatment group and to 13.3 mm Hg for the standard eye drop treatment group. There were no statistically significant differences in IOP reduction between groups.

E. Discussion and Conclusion

The pilot trials data reported herein demonstrate the pharmacodynamic equivalence of a 9.2 µl dose volume delivered by the AcuStream™ device to a 30 µl dose volume for standard eye drops (a factor of 3.3× greater volume), for two medications: a combination formulation of tropicamide (1% w/v) and phenylephrine (2.5% w/v) for pupil dilation, and latanoprost (0.005% w/v) formulation for intraocular pressure reduction.

Patient comfort is an important component of adherence and compliance with prescribed medical therapies. Video analysis of patient responses during and immediately after drug administration and the patients' indication of comfort on the visual analog comfort scale show a favorable improvement in patient comfort when the AcuStream™ device was used compared with standard eye drops. Slit lamp examination and fluorescein staining revealed no evidence of epithelial disruption due to drug administration via the AcuStream™ device.

The pilot trials results demonstrate that the AcuStream™ device is a safe, effective and comfortable alternative to the use of standard eye drop administration. The results from both trials demonstrate that the AcuStream™ device is an equally effective alternative to standard eye drop delivery as demonstrated by comparable effects on pupil dilation and intraocular pressure, while delivering less than one-third of the volume. Feedback from the patients also indicate that delivery with AcuStream™ is more comfortable.

Aspects, including embodiments, of the subject matter described herein may be beneficial alone or in combination, with one or more other aspects or embodiments. Without limiting the description, certain non-limiting aspects of the disclosure numbered 1-96 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of administering an ophthalmic agent to a topical ocular location of an eye of a subject, the method comprising:
   delivering to the topical ocular location a dose of a liquid formulation of the ophthalmic agent that can be wholly incorporated into the tear film of the eye.
2. The method according to Clause 1, wherein the dose is delivered as a stream to the topical ocular location.
3. The method according to any of Clauses 1 to 2, wherein a known amount of ophthalmic agent is delivered to the topical ocular location.
4. The method according to any of Clauses 1 to 3, wherein the amount of ophthalmic agent delivered and retained on the ocular location has a mass equal to the administered volume times the concentration of ophthalmic agent in the liquid formulation of the micro-dose.
5. The method according to any of the preceding clauses, wherein the delivered dose has a volume ranging from 1 to 15 µl.

6. The method according to Clause 5, wherein the delivered dose has a volume ranging from 3 to 10 μl.
7. The method according to any of the preceding clauses, wherein the delivered dose is administered by a handheld device.
8. The method according to Clause 7, wherein the handheld device comprises:
   a container comprising the liquid formulation and an aperture; and
   an actuator configured to emit the delivered dose from the container through the aperture.
9. The method according to any of the preceding clauses, wherein the method is a method of treating the subject for an ocular condition.
10. The method according to any of Clauses 1 to 8, wherein the liquid formulation is preservative free.
11. A method of treating a subject for an ocular condition, the method comprising:
   delivering to a topical ocular location of the subject a micro-dose of an ophthalmic agent liquid formulation effective to treat the subject for the ocular condition.
12. The method according to Clause 11, wherein the micro-dose has a volume ranging from 1 to 15 μl.
13. The method according to Clause 12, wherein the micro-dose has a volume ranging 3 to 10 μl.
14. The method according to any of Clauses 11 to 13, wherein a known amount of ophthalmic agent is delivered to the topical ocular location.
15. The method according to any of Clauses 11 to 14, wherein the amount of ophthalmic agent delivered and retained on the ocular location has a mass equal to the administered volume times the concentration of ophthalmic agent in the liquid formulation of the micro-dose.
16. The method according to Clause 15, wherein the amount of ophthalmic agent delivered to the topical ocular location is determined from pulse duration and ophthalmic agent concentration in the liquid formulation.
17. The method according to any of Clauses 11 to 16, wherein the micro-dose is administered as a single stream.
18. The method according to Clause 17, wherein the stream is continuous.
19. The method according to Clause 18, wherein the stream is discontinuous.
20. The method according to any of the Clauses 11 to 16, wherein the micro-dose is administered as a series of streams.
21. The method according to any of Clauses 11 to 16, wherein the micro-dose is administered as a plurality of droplets.
22. The method according to any of Clauses 11 to 21, wherein the micro-dose is self-administered.
23. The method according to any of Clauses 11 to 22, wherein the micro-dose is administered by a handheld device.
24. The method according to Clause 23, wherein the handheld device comprises:
   a container comprising a liquid formulation of the ophthalmic agent; and
   an actuator configured to emit the micro-dose from the container through the aperture.
25. The method according to Clause 24, wherein the container comprises a volume of the liquid formulation sufficient to provide multiple micro-doses.
26. The method according to any of Clauses 11 to 25, wherein the ophthalmic agent is a cholinergic agent.
27. The method according to Clause 26, wherein the cholinergic agent is a muscarinic agonist.
28. The method according to Clause 27, wherein the muscarinic agonist is selected from the group consisting of: pilocarpine, carbochol, physostigmine, methacholine and pharmaceutically acceptable salts thereof, and combinations thereof.
29. The method according to any of Clauses 11 to 25, wherein the ophthalmic agent is a miotic agent.
30. The method according to clause 29, wherein the ophthalmic agent is selected from the group consisting of: pilocarpine, carbochol, physostigmine, echothiophate, methacholine, moxisylyte and pharmaceutically acceptable salts thereof, and combinations thereof.
31. The method according to any of Clauses 11 to 30, wherein ocular condition is presbyopia.
32. The method according to any of Clauses 11 to 30, wherein the ocular condition is glaucoma.
33. The method according to Clause 32, wherein the glaucoma is angle-closure glaucoma.
34. The method according to any of Clauses 11 to 30, wherein the ocular condition is dry eye.
35. The method according to any of Clauses 11 to 30, wherein the ocular condition is selected from:
   Sjogren's Syndrome associated with ocular discomfort or dryness or both;
   a refractive error including hyperopia and astigmatism; and
   post-surgical optical aberration, e.g., following cataract surgery, keratorefractive surgery, and corneal transplantation.
36. The method according to any of Clauses 11 to 25, wherein the active agent comprises an intraocular pressure modulatory agent.
37. The method according to Clause 36, wherein the ocular condition is glaucoma.
38. The method according to any of Clauses 11 to 37, wherein the liquid formulation is preservative free.
39. A method of treating a subject for presbyopia, the method comprising:
   delivering to a topical ocular location of the subject a micro-dose of a miotic agent effective to treat the subject for presbyopia without substantial adverse effects.
40. The method according to Clause 39, wherein the micro-dose has a volume ranging from 1 to 15 μl.
41. The method according to Clause 40, wherein the micro-dosage has a volume ranging from 3 to 10 μl.
42. The method according to any of Clauses 39 to 41, wherein the miotic agent is selected from the group consisting of: pilocarpine, carbochol, physostigmine, echothiophate, methacholine, moxisylyte and pharmaceutically acceptable salts thereof, and combinations thereof.
43. The method according to Clause 42, where the miotic agent is pilocarpine.
44. The method according to any of Clauses 39 to 43, wherein the miotic agent is the sole active agent in the micro-dose.
45. The method according to any of Clauses 39 to 44, wherein a known amount of the miotic agent is delivered to the topical ocular location.
46. The method according to any of Clauses 39 to 45, wherein the amount of miotic agent delivered to the topical ocular location has a mass equal to the administered volume times the concentration of cholinergic agent in the liquid formulation of the micro-dose.
47. The method according to Clause 46, wherein the amount of miotic agent delivered to the topical ocular location is determined from pulse duration and active agent concentration in the liquid formulation.
48. The method according to any of Clauses 39 to 47, wherein the method results in a reduction in pupil diameter ranging from 0.25 to 10 mm as compared with prior to drug administration.
49. The method according to any of Clauses 39 to 48, wherein the method results in improvement in visual acuity ranging from 2 to 6 lines on a Jaeger or Rosenbaum near card or ETDRS Near Chart.
50. The method according to any of Clauses 39 to 49, wherein the micro-dose is administered as a stream of the liquid formulation.
51. The method according to Clause 50, wherein the stream is continuous.
52. The method according to Clause 50, wherein the stream is discontinuous.
53. The method according to any of the Clauses 39 to 49, wherein the micro-dose is administered as a series of streams.
54. The method according to any of Clauses 39 to 49, wherein the micro-dose is administered as a plurality of droplets.
55. The method according to any of Clauses 39 to 54, wherein the micro-dose is self-administered.
56. The method according to any of Clauses 39 to 55, wherein the micro-dose is administered by a handheld device that comprises:
a container comprising a liquid formulation of the miotic agent and an aperture; and
an actuator configured to emit the micro-dose from the container through the aperture.
57. The method according to Clause 56, wherein the container comprises a volume of the liquid formulation sufficient to provide multiple micro-doses.
58. The method according to any of Clauses 39 to 57, wherein the liquid formulation is preservative-free.
59. A method of treating a subject for glaucoma, the method comprising:
delivering to a topical ocular location of an eye of the subject a dose of a liquid formulation of an intraocular pressure modulatory agent that can be wholly incorporated into the tear film of the eye to treat the subject for glaucoma.
60. The method according to Clause 59, wherein the delivered dose has a volume ranging from 1 to 15 μl.
61. The method according to Clause 60, wherein the delivered dose has a volume ranging from 3 to 10 μl.
62. The method according to any of Clauses 59 to 61, wherein the delivered dose is administered as a stream of the liquid formulation.
63. The method according to Clause 62, wherein the stream is continuous.
64. The method according to Clause 62, wherein the stream is discontinuous.
65. The method according any of Clauses 59 to 64, wherein the topical ocular location comprises a corneal/conjunctival location.
66. The method according to Clause 65, wherein the topical ocular location comprises an area ranging from 2.5 to 12 μm$^2$.
67. The method according to any of Clauses 59 to 66, wherein the delivered dose is self-administered.
68. The method according to any of Clauses 59 to 67, wherein the delivered dose is administered by a handheld device that comprises:
a container comprising the liquid formulation and an aperture; and
an actuator configured to emit the delivered dosage from the container through the aperture.
69. The method according to Clause 68, wherein the container comprises a volume of the liquid formulation sufficient to provide multiple delivered doses.
70. The method according to any of Clauses 59 to 69, wherein the liquid formulation is preservative free.
71. The method according to any of Clauses 59 to 70, wherein the intraocular pressure modulatory agent increases aqueous humor outflow.
72. The method according to Clause 71, wherein the intraocular pressure modulatory agent is a prostaglandin agent.
73. The method according to Clause 72, wherein the prostaglandin active agent is latanoprost.
74. The method according to any of Clauses 59 to 73, wherein the intraocular pressure modulatory agent decreases aqueous humor production.
75. The method according to Clause 74, wherein the intraocular pressure modulatory agent is a β-adrenergic receptor antagonist.
76. The method according to Clause 75, wherein the β-adrenergic receptor antagonist is timolol.
77. The method according to any of Clauses 59 to 76, wherein the delivered dosage has an efficacy comparable to a reference dosage having a volume that exceeds the capacity of tear film.
78. A device configured to deliver a dose of a liquid formulation of an ophthalmic agent to a topical ocular location of an eye of a subject, wherein the dose is wholly accommodated by the tear film of the eye.
79. The device according to Clause 78, wherein the dose has a volume ranging from 1 to 15 μl.
80. The device according to Clause 79, wherein the micro-dose has a volume ranging from 3 to 10 μl.
81. The device according to any of Clauses 78 to 80, wherein the ophthalmic agent is a cholinergic agent.
82. The device according to any of Clauses 78 to 80, wherein the ophthalmic agent is a miotic agent.
83. The device according to any of Clauses 78 to 80, wherein the ophthalmic agent is an intraocular pressure modulatory agent.
84. The device according to any of Clauses 78 to 83, wherein the device is configured to administer the dose as a stream of the liquid formulation.
85. The device according to Clause 84, wherein the stream is continuous.
86. The device according to Clause 84, wherein the stream is discontinuous.
87. The device according to any of Clauses 78 to 83, wherein the device is configured to administer the dose as a series of streams.
88. The device according to any of Clauses 78 to 83, wherein the device is configured to administer the dose as a plurality of droplets.
89. The device according to any of Clauses 78 to 88, wherein the device is a handheld device that comprises:
a container comprising a liquid formulation of the cholinergic agent and an aperture; and
an actuator configured to emit the dose from the container through the aperture.

90. The device according to any of Clauses 78 to 89, wherein the liquid formulation is preservative free.

91. The device according to Clause 90, wherein the container comprises a volume of the liquid formulation sufficient to provide multiple delivered doses.

92. A kit comprising a device according to any of Clauses 78 to 91.

93. A kit comprising a container comprising a liquid formulation of an ophthalmic agent, wherein the container is configured to be operably employed in a device according to any of Clauses 78 to 91.

94. The device according to Clause 93, wherein the ophthalmic agent is a cholinergic agent.

95. The device according to Clause 93, wherein the ophthalmic agent is a miotic agent.

96. The device according to Clause 93, wherein the ophthalmic agent is an intraocular pressure modulatory agent.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112 (f) or 35 U.S.C. § 112 (6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112 (6) is not invoked.

What is claimed is:

1. A method of treating a subject for an ophthalmic condition, the method comprising:
providing a handheld device having a volume of liquid, an aperture through which the liquid can be ejected as a stream towards a target eye of the subject, and a concave mirror disposed downstream of the aperture and having an opening through which fluid from the aperture can be directed;
moving the handheld device until the subject can observe an image of the target eye in the concave mirror becoming focused, indicating alignment of the handheld device with the target eye; and
activating an actuator engaging the handheld device to generate pressure fluctuations within the liquid inside the handheld device and to disengage a rod disposed within the handheld device from the aperture to unseal the aperture and administer the liquid, through the aperture, to the aligned target eye.

2. The method according to claim 1, wherein the activating step includes administering 3 to 10 µl of the liquid through the aperture.

3. The method according to claim 1, wherein the liquid does not include any agent that ameliorates an adverse effect of a therapeutic agent.

4. The method according to claim 3, wherein the therapeutic agent is a sole active agent in the liquid.

5. The method according to claim 1, wherein a concentration of a therapeutic agent within the liquid ranges from 50 ng/ml to 100 mg/ml.

6. The method according to claim 1, wherein a volume of a therapeutic agent delivered to the target eye is determined from pulse duration of the actuator and active agent concentration in the liquid.

7. The method according to claim 1, wherein the handheld device comprises a volume of the liquid sufficient to provide multiple applications.

8. The method according to claim 1, wherein the liquid is preservative-free.

9. The method of claim 1, wherein the ophthalmic condition is selected from the group consisting of: presbyopia, glaucoma, myopia, and dry eye.

10. The method of claim 1, wherein a radius of curvature of the concave mirror is in a range from 60 mm to 120 mm.

11. The method of claim 1, wherein a diameter of the concave mirror is in a range from 15 mm to 30 mm.

12. The method of claim 1, wherein a distance between the aperture and the target eye is in a range from 30 mm to 60 mm when the subject has properly aligned the handheld device using the mirror.

13. A method of delivering a liquid, the method comprising: providing a liquid delivery device having a reservoir containing the liquid, an aperture through which the liquid is ejected from the liquid delivery device, and a biasing mechanism to engage and create a seal with the aperture to prevent ingress of bacteria and contaminants through the aperture, and into the liquid delivery device, when liquid is not being ejected therethrough; and a concave mirror disposed downstream of the aperture and having an opening through which fluid from the aperture can be directed; and oscillating an actuator to 1) generate pressure fluctuations inside the reservoir and 2) disengage the biasing mechanism from the aperture; and ejecting the liquid as a stream through the aperture towards a site of interest as a result of the pressure fluctuations inside the liquid delivery device, such that a volume of liquid delivered to the site of interest is substantially known.

14. The method according to claim 13, wherein, in the step of providing, the liquid includes an ophthalmic agent having a concentration ranging from about 50 ng/ml to about 100 mg/ml.

15. The method according to claim 13 wherein, in the step of providing, the biasing mechanism is designed to engage, at a first end, the aperture to selectively seal the aperture and to be affixed, at a second end, to a flexible membrane to facilitate movement of the biasing mechanism relative to the aperture.

16. The method according to claim 13, wherein, in the step of providing, the biasing mechanism is moveable relative to the aperture between a first position that seals the aperture and a second position that permits liquid to be ejected through the aperture.

* * * * *